United States Patent [19]
Ries et al.

[11] Patent Number: 5,521,177
[45] Date of Patent: May 28, 1996

[54] BENZIMIDAZOLES, PHARMACEUTICAL COMPOSITIONS CONTAINING THESE COMPOUNDS AND PROCESSES FOR PREPARING THEM

[75] Inventors: Uwe Ries, Biberach; Norbert Hauel, Schemmerhofen; Jacques van Meel, Mlttelbiberach; Wolfgang Wienen, Äpfingen; Michael Entzeroth, Warthausen, all of Germany

[73] Assignee: Dr. Karl Thomae GmbH, Biberach an der Riss, Germany

[21] Appl. No.: 132,065

[22] Filed: Oct. 4, 1993

[30] Foreign Application Priority Data

Oct. 6, 1992 [DE] Germany .............. 42 33 590.6
May 8, 1993 [DE] Germany .............. 43 15 349.6

[51] Int. Cl.$^6$ .................. A61K 31/535; C07D 413/14
[52] U.S. Cl. .................. 514/231.2; 514/381; 514/394; 544/139; 548/252; 548/304.4
[58] Field of Search .................. 548/304.4, 252; 514/394, 231.2, 381; 544/139

[56] References Cited

FOREIGN PATENT DOCUMENTS 461039 12/1991 European Pat. Off. ............ 548/304.4
0502314 9/1992 European Pat. Off. ..

OTHER PUBLICATIONS

Young, R. et al., *J. Med. Chem.*, 29 (1986), 44–49.

*Primary Examiner*—Jacqueline Haley
*Attorney, Agent, or Firm*—Robert P. Raymond; Alan R. Stempel; Mary-Ellen M. Devlin

[57] ABSTRACT

The invention relates to benzimidazoles of general formula

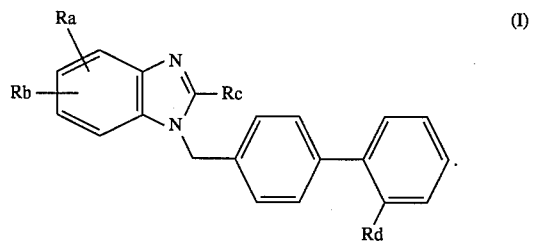

(I)

Exemplary compounds are:

(a) 4'-[[2-Ethyl-4-methyl-6-[(2-dimethylamino-3,4-dioxo-1-cyclobuten-1-yl)amino]-1H-benzimidazol-1-yl]-methyl]-2-(1H-tetrazol-5-yl)-biphenyl, (b) 4'-[[2-n-Propyl-4-methyl-6-(2-cyano-3,3-dimethylguanidino)-1H-benzimidazol-1-yl]-methyl]-2-(1H-tetrazol-5-yl)-biphenyl, (c) 4'-[[2-n-Propyl-4-methyl-6-(2,2-dicyano-1-dimethylamino-etheneamino)-1H-benzimidazol-1-yl]-methyl]-2-(1H-tetrazol-5-yl)-biphenyl, (d) 4'-[[2-n-Propyl-4-methyl-6-(1-morpholino-2-nitroetheneamino)-1H-benzimidazol-1-yl]-methyl]-2-(1H-tetrazol-5-yl)-biphenyl, and (e) 4'-[[2-n-Propyl-4-methyl-6-(1,1-dimethylamino-2-nitro-etheneamino)-1H-benzimidazol-1-yl]-methyl]-2-(1H-tetrazol-5-yl)-biphenyl.

The new compounds are angiotensin-antagonists.

14 Claims, No Drawings

BENZIMIDAZOLES, PHARMACEUTICAL COMPOSITIONS CONTAINING THESE COMPOUNDS AND PROCESSES FOR PREPARING THEM

The present invention relates to new benzimidazoles of general formula

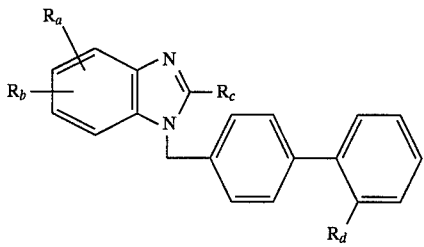

the 1-, 3-isomer mixtures thereof and the salts thereof, particularly for pharmaceutical use the physiologically acceptable salts thereof with inorganic or organic acids or bases which are valuable angiotensin antagonists, particularly angiotensin-II-antagonists, pharmaceutical compositions containing these compounds and the use thereof and processes for preparing them.

In general formula I above $R_a$ denotes a $C_{1-3}$-alkyl group, a trifluoromethyl group, a hydrogen, fluorine, chlorine or bromine atom, $R_b$ denotes an $R_1NH$— group in which the hydrogen atom is replaced by an R—CX— group, by a 3,4-dioxo-1-cyclobuten-1-yl group substituted in the 2-position by a $C_{1-3}$-alkoxy group or by an $(R_1NR_3)$— group, or by a 3-nitropyrrol-2-yl group, wherein the pyrrole group may additionally be substituted in the 1-position by a $C_{1-3}$-alkyl group, wherein R denotes a $C_{1-5}$-alkyl group, an alkoxy or alkylthio group each having 1 to 3 carbon atoms, a phenoxy or phenylthio group or an $(R_2NR_3)$— group and X denotes an $NO_2$—CH=, $(R_4R_5)C=$ or $R_6N=$ group, wherein $R_1$ denotes a hydrogen atom or a $C_{1-3}$-alkyl group, $R_2$ denotes a hydrogen atom, a branched or unbranched $C_{1-10}$-alkyl group which may be substituted in the 2-, 3- or 4-position by a hydroxy, alkoxy, amino, alkylamino or dialkylamino group, wherein the alkyl moiety in each case may contain 1 to 3 carbon atoms, a $C_{1-4}$-alkyl group which is substituted by a phenyl or pyridyl group and may additionally be substituted by a hydroxy group in the 2-, 3- or 4-position, a $C_{3-4}$-cycloalkyl group, a $C_{5-8}$-cycloalkyl group wherein an ethylene bridge may be replaced by an o-phenylene group, a $C_{6-8}$-bicycloalkyl group optionally substituted by 1, 2 or 3 alkyl groups, $R_3$ denotes a hydrogen atom or an alkyl group which may be substituted in the 2- or 3-position by an alkoxy, amino, alkylamino or dialkylamino group, wherein the above-mentioned alkyl and alkoxy moieties may each contain 1 to 3 carbon atoms, or $R_2$ and $R_3$ together with the nitrogen atom between them denote a cyclic $C_{4-6}$-alkyleneimino group (which may be substituted by one or two alkyl groups or by a phenyl group and wherein additionally an ethylene bridge in the 3,4-position may be replaced by an o-phenylene group), a morpholino group or a piperazino group optionally substituted in the 4-position by a $C_{1-3}$-alkyl group or by a phenyl group, $R_4$ and $R_5$, which may be identical or different, each denotes a cyano, $R_2NR_3$—CO— or alkoxycarbonyl group having a total of 2 to 5 carbon atoms, wherein $R_2$ and $R_3$ are as hereinbefore defined, and $R_6$ denotes a cyano, tetrazol-5-yl-, alkanesulphonyl, phenylsulphonyl, phenylalkanesulphonyl, aminosulphonyl, alkylaminosulphonyl, dialkylaminosulphonyl, alkylcarbonyl, phenylcarbonyl, aminocarbonyl, alkylaminocarbonyl or dialkylaminocarbonyl group wherein the alkyl moiety may contain 1 to 3 carbon atoms, $R_c$ denotes a $C_{2-4}$-alkyl group, an alkoxy or alkylthio group each having 2 or 3 carbon atoms in the alkyl moiety, or a cyclopropyl or cyclobutyl group and $R_d$ denotes a group which may be converted in vivo into a carboxy group, or it denotes a carboxy, cyano, 1H-tetrazolyl, 1-triphenylmethyl-tetrazolyl or 2-triphenylmethyl-tetrazolyl group.

The phrase "a group which is converted in vivo into a carboxy group" which appears above refers for example to the esters of formula

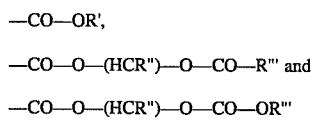

wherein

R' denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, R" denotes a hydrogen atom or a methyl group and R'" denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group.

Preferred compounds of general formula I above are those wherein $R_a$ denotes a methyl group or a hydrogen, fluorine, chlorine or bromine atom, $R_b$ denotes an $R_1NH$— group in which the hydrogen atom is replaced by an R—CX— group, by a 3,4-dioxo-1-cyclobuten-1-yl group (substituted in the 2-position by a $C_{1-3}$alkoxy group or by an $(R_1NR_3)$—group) or by a 3-nitropyrrol-2-yl group, whilst the pyrrolyl group may additionally be substituted in the 1-position by a methyl group, wherein R denotes a $C_{1-3}$-alkyl group, a methoxy, methylthio, phenoxy or phenylthio group or an $(R_2NR_3)$—group and X denotes an $NO_2$—CH=, $(NC)_2C=$ or $R_6$—N= group wherein $R_1$ denotes a hydrogen atom or a $C_{1-3}$-alkyl group, $R_2$ denotes a $C_{1-3}$-alkyl group which may be substituted in the 2- or 3-position by a hydroxy, alkoxy, amino, alkylamino or dialkylamino group, whilst the alkoxy and alkyl moieties may each contain 1 to 3 carbon atoms, or $R_2$ denotes a $C_{5-7}$-cycloalkyl group, $R_3$ denotes a hydrogen atom, a $C_{1-3}$-alkyl group, a 2-methoxyethyl, 2-dimethylaminoethyl or 2-diethylaminoethyl group or $R_2$ and $R_3$ together with the nitrogen atom between them denote a cyclic $C_{4-5}$-alkyleneimino group (which may be substituted by one or two methyl groups), a morpholino group or a piperazino group optionally substituted in the 4-position by a $C_{1-3}$-alkyl group and $R_6$ denotes an alkylsulphonyl group having 1 to 3 carbon atoms in the alkyl moiety or a cyano, aminosulphonyl or phenylsulphonyl group, $R_c$ denotes a $C_{2-4}$-alkyl group and $R_d$ denotes a carboxy, 1H-tetrazolyl, 1-triphenylmethyltetrazolyl or 2-triphenylmethyl-tetrazolyl group, the 1-, 3-isomer mixtures thereof and the salts thereof.

Particularly preferred compounds of general formula I above are those wherein $R_a$ in the 4-position denotes a methyl group or a chlorine atom, $R_b$ in the 6-position denotes an $R_1NH$— group in which the hydrogen atom is replaced by an R—CX— group, by a 3,4-dioxo-1-cyclobuten-1-yl group substituted in the 2-position by an $(R_1NR_3)$—group, or by a 3-nitro-pyrrol-2-yl group, whilst the pyrrolyl group may additionally be substituted in the 1-position by a methyl group, wherein R denotes an $(R_2NR_3)$—group or a $C_{1-3}$-alkyl group and X denotes an $N_2$—CH=, $(NC)_2C$= or $R_6$—N= group wherein $R_1$ denotes a hydrogen atom or a methyl group, $R_2$ denotes a $C_{1-3}$-alkyl group, a 2-hydroxyethyl, 2-methoxyethyl, 2-dimethylaminoethyl or 2-diethylaminoethyl group or a $C_{5-7}$-cycloalkyl group, $R_3$ denotes a hydrogen atom, a $C_{1-3}$-alkyl group, a 2-methoxyethyl, 2-dimethylaminoethyl or 2-diethylaminoethyl group or $R_2$ and $R_3$ together with the nitrogen atom between them denote a pyrrolidino, piperidino, morpholino or 4-methyl-piperazino group and $R_6$ denotes a cyano, aminosulphonyl, methylsulphonyl or phenylsulphonyl group, $R_c$ denotes a $C_{2-4}$-alkyl group and $R_d$ denotes a carboxy or 1H-tetrazolyl group, particularly the compounds (a) 4'-[[2-n-propyl-4-methyl-6-(2-cyano-3-methyl-guanidino) -1H-benzimidazol-1-yl]-methyl]-biphenyl-2-carboxylic acid, (b) 4'-[[2-n-propyl-4-methyl-6-(2-cyano-3,3-dimethyl-guanidino) -1H-benzimidazol-1-yl]-methyl]-2-(1H-tetrazol-5-yl)-biphenyl, (c) 4'-[[2-n-propyl-4-methyl-6-(2,2-dicyano-1-dimethylamino-ethyleneamino) -1H-benzimidazol-1-yl]methyl]-biphenyl-2-carboxylic acid, (d) 4'-[[2-n-propyl-4-methyl-6-(1-dimethylamino-2-nitroethyleneamino) -1H-benzimidazol-1-yl]methyl]-biphenyl-2-carboxylic acid, (e) 4'-[[2-n-propyl-4-methyl-6-(3-methyl-2-amidosulphonyl-guanidino) -1H-benzimidazol-1-yl]methyl]-biphenyl-2-carboxylic acid, (f) 4'-[[2-n-propyl-4-methyl-6-(1,1-dimethylamino-2-nitroethyleneamino) -1H-benzimidazol-1-yl]-methyl]-2-(1H-tetrazol-5-yl)-biphenyl, (g) 4'-[[2-ethyl-4-methyl-6-[(2-dimethylamino-3,4-dioxo-1-cyclobuten-1-yl) -amino]-1H-benzimidazol-1-yl]-methyl]-biphenyl-2-carboxylic acid and (h) 4'-[[2-ethyl-4-methyl-6-(3,3-dimethyl-2-methylsulphonyl-guanidino) -1H-benzimidazol-1-yl]methyl]-2-(1H-tetrazol-5-yl)-biphenyl, the 1-, 3-isomer mixtures thereof and the salts thereof.

According to the invention the compounds are obtained by the following processes:

a) In order to prepare compounds of general formula I wherein R denotes an alkoxy or alkylthio group, each having 1 to 3 carbon atoms, or a phenyloxy or phenylthio group:

Reaction of a compound of general formula

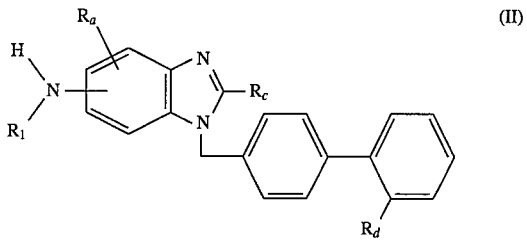

(II)

wherein $R_a$, $R_c$, $R_d$ and $R_1$ are as hereinbefore defined, with a compound of general formula $(Y')_2C$=x (III)

wherein

X is as hereinbefore defined, the groups Y', which may be identical or different, each denote an alkoxy or alkylthio group having 1 to 3 carbon atoms, or a phenoxy or phenylthio group.

The reaction is preferably carried out in a solvent such as methanol, ethanol, isopropanol, dioxane, tetrahydrofuran or chloroform, optionally in the presence of an acid-binding agent such as potassium carbonate, triethylamine or pyridine, whilst the latter two may also be used as solvents, appropriately at temperatures between 0° and 50° C., but preferably at ambient temperature.

b) In order to prepare compounds of general formula I wherein R denotes an $(R_2NR_3)$—group:

Reaction of a compound of general formula

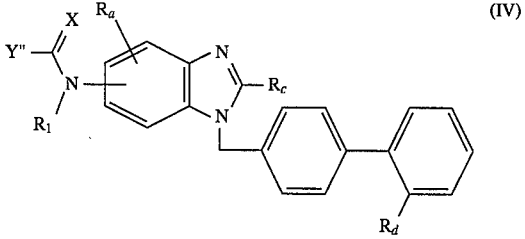

(IV)

(wherein $R_a$, $R_c$, $R_d$, $R_1$ and X are as hereinbefore defined and Y" denotes an alkoxy, alkylthio, alkylsulphinyl or alkylsulphonyl group each having 1 to 3 carbon atoms, or Y" denotes a phenyloxy, phenylthio, phenylsulphinyl or phenylsulphonyl group) with an amine of general formula $R_2R_3H$ (V)

wherein $R_2$ and $R_3$ are as hereinbefore defined.

The reaction is preferably carried out in a solvent such as ethanol, isopropanol, tetrahydrofuran, dioxane or benzene or in an excess of the amine of general formula V used, optionally in a pressurised vessel and optionally in the presence of a base such as sodium carbonate, potassium carbonate, triethylamine or pyridine at temperatures between 0° and 125° C., preferably at temperatures between 50° and 100° C.

If Y" in a compound of general formula IV denotes an alkylthio- or phenylthio group, the corresponding sulphinyl compound is conveniently obtained by previous oxidation with an oxidising agent or if Y" in a compound of general formula IV denotes an alkylthio, alkylsulphinyl, phenylthio or phenylsulphinyl group, the corresponding sulphonyl compound is conveniently obtained by previous oxidation with an oxidising agent.

The previous oxidation is carried out with an oxidising agent such as a peracid, e.g. 3-chloroperbenzoic acid, in a solvent such as methylene chloride, ethanol, isopropanol, tetrahydrofuran, dioxane or benzene at temperatures between 0° and 50° C., preferably at ambient temperature.

c) In order to prepare compounds of general formula I wherein R denotes a $C_{1-5}$-alkyl group:

Reaction of a compound of general formula

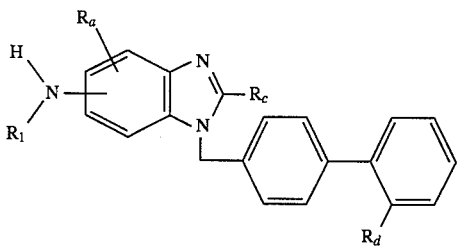

wherein $R_a$, $R_c$, $R_d$ and $R_1$ are as hereinbefore defined, with a compound of general formula

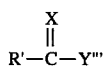

wherein X is as hereinbefore defined,
R' denotes a $C_{1-5}$-alkyl group and
Y''' denotes a $C_{1-3}$-alkylthio group.

The reaction is preferably carried out in a solvent such as methanol, ethanol, isopropanol, dioxane, tetrahydrofuran or chloroform, optionally in the presence of an acid binding agent such as potassium carbonate, triethylamine or pyridine, whilst the latter two may also be used as solvents, appropriately at temperatures between 0° and 50° C., but preferably at ambient temperature.

d) In order to prepare a compound of general formula I wherein $R_d$ denotes a carboxy group:

Conversion of a compound of general formula

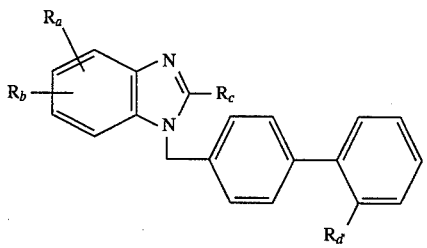

wherein $R_a$ to $R_c$ are as hereinbefore defined and $R_d'$ denotes a group which may be converted into a carboxy group by hydrolysis, thermolysis or hydrogenolysis.

For example, functional derivatives of the carboxy group such as the unsubstituted or substituted amides, esters, thiolesters, orthoesters, iminoethers, amidines or anhydrides, the nitrile group or the tetrazolyl group may be converted by hydrolysis into a carboxy group; esters with tertiary alcohols, e.g. the tert.butylester, may be converted by thermolysis into a carboxy group; and esters with aralkanols, e.g. the benzylester, may be converted by hydrogenolysis into a carboxy group.

The hydrolysis is appropriately carried out either in the presence of an acid such as hydrochloric acid, sulphuric acid, phosphoric acid, trichloroacetic acid or trifluoroacetic acid or, most advantageously, in the presence of a base such as sodium hydroxide or potassium hydroxide, in a suitable solvent such as water, water/methanol, ethanol, water/ethanol, water/isopropanol or water/dioxane, at temperatures between −10° C. and 120° C., e.g. at temperatures between ambient temperature and the boiling temperature of the reaction mixture.

If $R_d'$ in a compound of general formula VII represents a cyano or aminocarbonyl group, these groups may also be converted into the carboxy group with a nitrite, e.g. sodium nitrite, in the presence of an acid such as sulphuric acid, which may simultaneously also be used as solvent, at temperatures between 0° and 50° C.

If $R_d'$ in a compound of general formula VII represents for example a tert.-butyloxycarbonyl group, the tert.-butyl group may also be thermally cleaved, optionally in an inert solvent such as methylene chloride, chloroform, benzene, toluene, tetrahydrofuran or dioxane and preferably in the presence of a catalytic amount of an acid such as trifluoroacetic acid, p-toluenesulphonic acid, sulphuric acid, phosphoric acid or polyphosphoric acid, preferably at the boiling temperature of the solvent used, e.g. at temperatures between 40° C. and 100° C.

If $R_d'$ in a compound of general formula VII represents, for example, a benzyloxycarbonyl group, the benzyl group may also be hydrogenolytically cleaved in the presence of a hydrogenation catalyst such as palladium/charcoal, in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar. During hydrogenolysis, other groups may be reduced at the same time, e.g. a nitro group may be reduced to the amino group, a benzyloxy group to a hydroxy group, a vinylidene group to the corresponding alkylidene group or a cinnamic acid group to the corresponding phenyl-propionic acid group, or they may be replaced by hydrogen atoms, e.g. a halogen atom may be replaced by a hydrogen atom.

e) In order to prepare a compound of general formula I wherein $R_d$ represents a 1H-tetrazolyl group:

Cleaving a protecting group from a compound of general formula

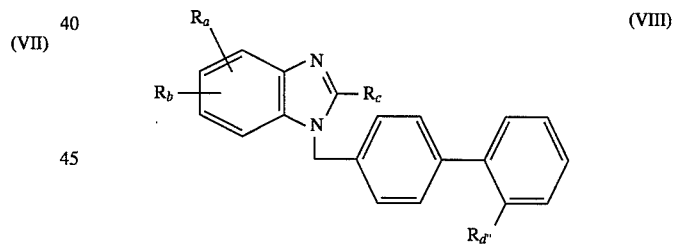

wherein
$R_a$ to $R_c$ are defined as hereinbefore and $R_d''$ represents a 1H-tetrazolyl or 2H-tetrazolyl group protected in the 1- or 2-position by a protecting group.

Suitable protecting groups include, for example, the triphenylmethyl, tributyl tin or triphenyl tin groups.

The cleaving of a protecting group used is preferably carried out in the presence of a hydrohalic acid, preferably in the presence of hydrochloric acid, in the presence of a base such as sodium hydroxide or alcoholic ammonia, in a suitable solvent such as methylene chloride, methanol, methanol/ammonia, ethanol or isopropanol, at temperatures between 0° and 100° C., but preferably at ambient temperature or, if the reaction is carried out in the presence of alcoholic ammonia, at elevated temperatures, e.g. at temperatures between 100° and 150° C., preferably at temperatures between 120° and 140° C.

f) In order to prepare compounds of general formula I wherein $R_b$ denotes an $R_1NH—$ group in which the hydrogen atom is replaced by one of the above-mentioned 3-nitro-pyrrol-2-yl groups:

Cyclising a compound of general formula

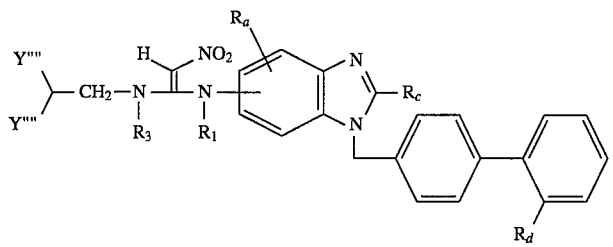

(IX)

optionally formed in the reaction mixture, wherein $R_1$, $R_3$, $R_a$, $R_c$ and $R_d$ are as hereinbefore defined and the groups $Y''''$ which may be identical or different, each represent a $C_{1-3}$-alkoxy group.

The cyclisation is preferably carried out in a solvent such as methanol, ethanol, isopropanol, tetrahydrofuran, dioxane or water or in aqueous mixtures thereof, in the presence of an acid such as hydrochloric acid or sulphuric acid at temperatures between 0° and 125° C., preferably at temperatures between 50° and 100° C. The compound of general formula IX required for this is conveniently obtained by reacting a corresponding compound of general formula IV with a 2-aminoacetaldehyde diacetal in a solvent such as ethanol, isopropanol, tetrahydrofuran, dioxane or benzene or in an excess of the 2-amino-acetaldehyde diacetal used, optionally in the presence of a base such as sodium carbonate, potassium carbonate, triethylamine or pyridine at temperatures between 0° and 125° C., preferably at temperatures between 50° and 100° C.

g) In order to prepare compounds of general formula I wherein $R_b$ denotes an $R_1NH$— group wherein the hydrogen atom is replaced by one of the above-mentioned 3,4-dioxo-1-cyclobuten-1-yl groups:

Reacting a compound of general formula

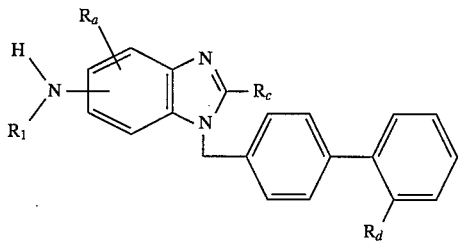

(II)

wherein $R_a$, $R_c$, $R_d$ and $R_1$ are as hereinbefore defined, with a 3,4-dioxo-1,3-dialkoxy-1-cyclobutene having 1 to 3 carbon atoms in the alkoxy moiety and in order to prepare a corresponding 2-amino compound subsequently reacting a 2-alkoxy compound thus obtained with an amine of general formula $R_2R_3NH$ (V)

wherein $R_2$ and $R_3$ are as hereinbefore defined.

The reaction is preferably carried out in a solvent such as methanol, ethanol, isopropanol, dioxane, tetrahydrofuran or chloroform, optionally in the presence of an acid binding agent such as potassium carbonate, triethylamine or pyridine, whilst the latter two may also be used as solvent, appropriately at temperatures between 0° and 50° C., but preferably at ambient temperature.

The subsequent reaction of a 2-alkoxy compound thus obtained with an amine of general formula V is preferably carried out in a solvent such as ethanol, isopropanol, tetrahydrofuran, dioxane or benzene or in an excess of the amine of general formula V used, optionally in a pressurised vessel and optionally in the presence of a base such as sodium carbonate, potassium carbonate, triethylamine or pyridine at temperatures between 0° and 125° C., preferably at temperatures between 50° and 100° C.

h) In order to prepare a compound of general formula I wherein $R_d$ denotes a 1H-tetrazolyl group:

Reacting a compound of general formula

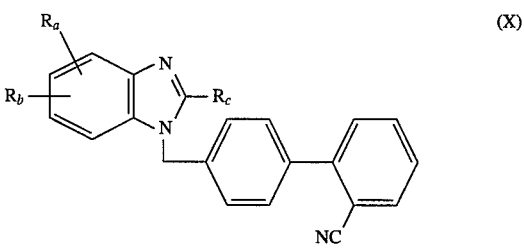

(X)

wherein $R_a$ to $R_c$ are as hereinbefore defined, with hydrazoic acid or the salts thereof.

The reaction is preferably carried out in a solvent such as benzene, toluene or dimethylformamide, at temperatures between 80° and 150° C., preferably at 125° C. Advantageously, either the hydrazoic acid is liberated during the reaction from an alkali metal azide, e.g. from sodium azide, in the presence of a weak acid such as ammonium chloride, or the tetrazolide salt obtained in the reaction mixture by reacting with a salt of hydrazoic acid, preferably with aluminium azide or tributyl tin azide, which are also conveniently prepared in the reaction mixture by reacting aluminium chloride or tributyl tin chloride with an alkali metal azide such as sodium azide, is subsequently liberated by acidification with a dilute acid such as 2N hydrochloric acid or 2N sulphuric acid.

In the reactions described hereinbefore, any reactive groups present such as hydroxy, amino or alkylamino groups may be protected during the reaction by means of conventional protecting groups which are split off again after the reaction.

By way of example, protecting groups for a hydroxy group may include the trimethylsilyl, acetyl, benzoyl, methyl, ethyl, tert.butyl, benzyl or tetrahydropyranyl groups and protecting groups for an amino, alkylamino or imino group may include an acetyl, benzoyl, ethoxycarbonyl or benzyl group.

The optional subsequent cleaving of a protecting group used is preferably carried out by hydrolysis in an aqueous solvent, e.g. in water, isopropanol/water, tetrahydrofuran/water or dioxane/water, in the presence of an acid such as hydrochloric acid or sulphuric acid or in the presence of an alkali metal base such as sodium hydroxide or potassium hydroxide, at temperatures between 0° and 100° C., preferably at the boiling temperature of the reaction mixture. However, a benzyl group is preferably cleaved by hydrogenolysis, e.g. with hydrogen in the presence of a catalyst such as palladium/charcoal, in a solvent such as methanol, ethanol, ethyl acetate or glacial acetic acid, optionally with the addition of an acid such as hydrochloric acid, at temperatures between 0° and 50° C., but preferably at ambient temperature, and under a hydrogen pressure of from 1 to 7 bar, but preferably from 3 to 5 bar.

An isomer mixture of a compound of general formula I thus obtained may if desired be resolved by chromatography using a substrate such as silica gel or aluminium oxide.

Moreover, the compounds of general formula I obtained may be converted into the acid addition salts thereof, more particularly for pharmaceutical use into the physiologically acceptable salts thereof with inorganic or organic acids. Suitable acids for this purpose include hydrochloric acid, hydrobromic acid, sulphuric acid, phosphoric acid, fumaric acid, succinic acid, lactic acid, citric acid, tartaric acid or maleic acid.

Furthermore, the new compounds of general formula I thus obtained, if they contain a carboxy or 1H-tetrazolyl group, may if desired subsequently be converted into the salts thereof with inorganic or organic bases, more particularly for pharmaceutical use into the physiologically acceptable salts thereof. Suitable bases include for example sodium hydroxide, potassium hydroxide, cyclohexylamine, ethanolamine, diethanolamine and triethanolamine.

The compounds of general formulae II to X used as starting materials are known from the literature in some cases or may be obtained by methods known from the literature, such as those described for example in EP-A-253310, EP-A-291969, EP-A-392317, EP-A-468470 and EP-A-502314.

Thus, for example, a compound of general formula II is obtained by cleaving a protecting group from a correspondingly substituted amino compound, which is in turn obtained by acylating a corresponding o-phenylenediamine and subsequent cyclisation or by acylating a corresponding o-amino-nitro compound, subsequent reduction of the nitro compound and cyclisation, whilst an NH-benzimidazole optionally obtained in this manner may be converted by alkylation with a corresponding biphenyl derivative into a compound which is correspondingly substituted in the 1-position, with optional subsequent cleaving of any protecting group used.

A compound of general formula IV used as starting material is obtained by reacting a compound of general formula II with a corresponding compound of general formula III, and a compound of general formulae VII and VIII is obtained by reacting a corresponding 1H-benzimidazole with a corresponding biphenyl derivative.

If the group $R_b$ in a starting compound of general formula VII or VIII contains one of the above-mentioned 3-nitropyrrole groups, this is obtained by reacting a corresponding 1-alkylmercapto-2-nitro-ethyleneamino compound with a corresponding 2-amino-acetaldehyde acetal and subsequent cyclisation in the presence of an acid (see also J. Med. Chem. 31, 669 (1988)).

If the group $R_b$ in a starting compound of general formula VII or VIII contains one of the above-mentioned 3,4-dioxo-1-cyclobutene groups, it is obtained by reacting a corresponding amino compound with a 1,2-dialkoxy-3,4-dioxo-1-cyclobutene and subsequently reacting with a corresponding amine (see also J. Med. Chem. 35, 4720 (1992)).

A starting compound of general formula IX is obtained by reacting a corresponding 1-alkylmercapto-2-nitroethyleneamine of general formula I with a 2-aminoacetaldehyde diacetal.

A compound of general formula VI used as starting material is obtained by reacting a correspondingly substituted dialkylthio compound with a corresponding alkylmagnesium halide.

The monoalkylation of amines which may be necessary to prepare the starting compounds is described in J. Chem. Soc. Chem. Com. 1984, 1335.

The new compounds of general formula I wherein $R_d$ denotes a group which can be converted into a carboxy group in vivo, or a carboxy or 1H-tetrazolyl group, and the physiologically acceptable salts thereof have valuable pharmacological properties. They are angiotensin antagonists, particularly angiotensin-II-antagonists. The other compounds of general formula I are valuable intermediates for preparing the above-mentioned compounds.

For example, the following compounds:

A=4'-[[2-n-propyl-4-methyl-6-(2-cyano-3-methyl-guanidino) -1H-benzimidazol-1-yl)-methyl]-biphenyl-2-carboxylic acid, B=4'-[[2-n-propyl-4-methyl-6-(2-cyano-3,3-dimethyl-guanidino) -1H-benzimidazol-1-yl]-methyl]-2-(1H-tetrazol-5-yl)-biphenyl, C=4'-[[2-n-propyl-4-methyl-6-(2,2-dicyano-1-dimethylamino-ethyleneamino) -1H-benzimidazol-1-yl]-methyl]-biphenyl-2-carboxylic acid, D=4'-[[2-n-propyl-4-methyl-6-(1-dimethylamino-2-nitro-etheneamino) -1H-benzimidazol-1-yl]methyl]-biphenyl-2-carboxylic acid, E=4'-[[2-n-propyl-4-methyl-6-(3-methyl-2-amidosulphonylguanidino) -1H-benzimidazol-1-yl]methyl]-biphenyl-2-carboxylic acid, F=4'-[[2-n-propyl-4-methyl-6-(1,1-dimethylamino-2-nitro-etheneamino) -1H-benzimidazol-1-yl]-methyl]-2-(1H-tetrazol-5-yl)-biphenyl, G=4'-[[2-ethyl-4-methyl-6-[(2-dimethylamino-3,4-dioxo-1-cyclobuten-1-yl) -amino]-1H-benzimidazol-1-yl]-methyl]-biphenyl-2-carboxylic acid and H=4'-[[2-ethyl-4-methyl-6-(3,3-dimethyl-2-methylsulphonyl-guanidino) -1H-benzimidazol-1-yl]methyl]-2-(1H-tetrazol-5-yl)-biphenyl were investigated for their biological activities as follows:
Description of Method: Angiotensin-II-Receptor Bonding The tissue (rat's lung) is homogenised in Tris buffer (50 mMol Tris, 150 mMol NaCl, 5 mMol EDTA, pH 7.40) and centrifuged twice for 20 minutes each time at 20,000×g. The finished pellet is resuspended in incubation buffer (50 mMol Tris, 5 mMol $MgCl_2$, 0.2% BSA, pH 7.40) 1:75, based on the moist weight of the tissue. Each 0.1 ml of homogenate is incubated for 60 minutes at 37° C. with 50 pM [$^{125}$I]-angiotensin-II (NEN, Dreieich, FRG) and increasing concentrations of the test substance in a total volume of 0.25 ml. The incubation is ended by rapid filtration through glass fibre filter mats. The filters are each washed with 4 ml of ice cold buffer (25 mMol Tris, 2.5 mMol $MgCl_2$, 0.1% BSA, pH 7.40). The bound radioactivity is measured in a gamma-counter. The corresponding $IC_{50}$ value is determined from the dosage-activity curve.

Substances A to H show the following $IC_{50}$ values in the test described:

| Substance | $IC_{50}$ [nM] |
|---|---|
| A | 11 |
| B | 3 |
| C | 64 |
| D | 13 |
| E | 56 |
| F | 2 |
| G | 17 |
| H | 4 |

Moreover, when the above compounds were administered in doses of up to 30 mg/kg i.v. no toxic side effects were observed, e.g. negative inotropic effects or heart rhythm disorders. The compounds are therefore well tolerated.

In view of their pharmacological properties, the new compounds and the physiologically acceptable salts thereof are suitable for the treatment of hypertension and cardiac insufficiency and also for treating ischaemic peripheral circulatory disorders, myocardial ischaemia (angina), for the prevention of the progression of cardiac insufficiency after myocardial infarct and for treating diabetic nephropathy, glaucoma, gastrointestinal diseases and bladder diseases.

Furthermore, the new compounds and the physiologically acceptable salts thereof are suitable for treating pulmonary diseases, e.g. lung oedema and chronic bronchitis, for preventing arterial re-stenosis after angioplasty, for preventing thickening of the vascular walls after vascular operations, arteriosclerosis and diabetic angiopathy. Because of the effect of angiotensin on the release of acetylcholine and dopamine in the brain, the new angiotensin antagonists are also suitable for alleviating central nervous system disorders, e.g. depression, Alzheimer's disease, Parkinson's syndrome and bulimia, as well as disorders of cognitive functions.

The dosage required to achieve these effects in adults is appropriately, when administered intravenously, 0.5 to 100 mg, preferably 1 to 70 mg, and, when administered orally, 0.1 to 200 mg, preferably 1 to 100 mg, 1 to 3 times a day. For this purpose, the compounds of general formula I prepared according to the invention, optionally in conjunction with other active substances such as, for example, hypotensive agents, ACE inhibitors, diuretics and/or calcium antagonists, may be incorporated together with one or more inert conventional carriers and/or diluents, e.g. with corn starch, lactose, glucose, micro-crystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat, or suitable mixtures thereof, in conventional galenic preparations such as plain or coated tablets, capsules, powders, suspensions or suppositories.

Examples of additional active substances which may be used in the combinations mentioned above include bendroflumethiazide, chlorothiazide, hydrochlorothiazide, spironolactone, benzothiazide, cyclothiazide, ethacrinic acid, furosemide, metoprolol, prazosin, atenolol, propranolol, (di)hydralazinehydrochloride, diltiazem, felodipine, nicardipine, nifedipine, nisoldipine, nitrendipine, captopril, enalapril, lisinopril, cilazapril, quinapril, fosinopril and ramipril. The dosage of these active substances is conveniently ⅕ of the lowest dose normally recommended up to ¼ of the normally recommended dosage, that is for example 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipine or 5 to 60 mg of nitrendipine.

The Examples which follow are intended to illustrate the invention:

EXAMPLE 1

4'-[[2-n-Propyl-4-chloro-6-(2-cyano-3-methyl-guanidino)-1H -benzimidazol-1-yl]-methyl]-biphenyl-2-carboxylic acid a) Methyl 4'-[(2-n-propyl-4-chloro-6-phthalimido-1H-benzimidazol-1-yl) -methyl]-biphenyl-2-carboxylate 3.27 g (10.0 mMol) of 2-n-propyl-4-chloro-6-phthalimido-1H-benzimidazole are dissolved in 50 ml of dimethylsulphoxide, 1.23 g (11.0 mMol) of potassium tert.butoxide are added in batches thereto and the resulting mixture is stirred for 30 minutes at ambient temperature. Then 3.38 g (11.0 mMol) of methyl 4'-bromomethyl-biphenyl-2-carboxylate are added in batches thereto. The reaction mixture is then stirred for 3 hours at ambient temperature, stirred into ice water and extracted 3 times with ethyl acetate. The combined organic phases are washed with saline solution and dried over magnesium sulphate. Then the solvent is removed in vacuo and the residue is chromatographed on silica gel (particle size 0.032–0.063 mm), using as eluant first petroleum ether and then mixtures of petroleum ether and ethyl acetate of increasing polarity (9:1, 4:1 and 7:3). The uniform fractions are combined and evaporated down.

Yield: 2.15 g (38% of theory), Melting point: sintering from 118° C.

b) Methyl 4'-[(2-n-propyl-4-chloro-6-amino-1H-benzimidazol-1-yl) -methyl]-biphenyl-2-carboxylate 2.05 g of methyl 4'-[(2-n-propyl-4-chloro-6-phthalimido-1H -benzimidazol-1-yl)-methyl]-biphenyl-2-carboxylate are dissolved in 125 ml of ethanol and mixed with 5 ml of a 40% aqueous methylamine solution. The reaction mixture is stirred for 3 hours at ambient temperature and then stirred into saline solution. After extracting 3 times with ethyl acetate the combined organic phases are dried over sodium sulphate and evaporated down. The residue is stirred with petroleum ether/ether (1:4) for 24 hours, the solids formed are suction filtered and dried.

Yield: 745 mg (50% of theory), Melting point: 120°–121° C.

c) Methyl 4'-[[2-n-propyl-4-chloro-6-(2-cyano-3-methyl-guanidino)-1H -benzimidazol-1-yl]-methyl]-biphenyl-2-carboxylate 0.7 g (1.6 mMol) of methyl 4'-[[2-n-propyl-4-chloro-6-amino-1H -benzimidazol-1-yl]-methyl]-biphenyl-2-carboxylate and 395 mg (1.6 mMol) of diphenyl cyanocarbamidate are dissolved in 75 ml of isopropanol and stirred for 18 hours at ambient temperature. Then the mixture is filtered to remove the turbidity. The filtrate is combined with about 1 ml of gaseous methylamine in a pressurised vessel and heated to 100° C. for 4 hours. After cooling, the reaction mixture is evaporated down and the residue is combined with 100 ml of saline solution. After extracting 3 times with ethyl acetate, the combined organic phases are dried over sodium sulphate. The crude product is chromatographed on silica gel (particle size: 0.032–0.063 mm), using as eluant first methylene chloride and then methylene chloride/ethanol (50:1, 25:1 and 9:1). The uniform fractions are combined and evaporated down.

Yield: 205 mg (21% of theory), Melting point: >250° C. (decomp.)

d) 4'-[[2-n-Propyl-4-chloro-6-(2-cyano-3-methyl-guanidino)-1H -benzimidazol-1-yl]-methyl]-biphenyl-2-carboxylic acid 175 mg (0.34 mMol) of methyl 4'-[(2-n-propyl-4-chloro-6-(2-cyano-3-methyl-guanidino) -1H-benzimidazol-1-yl)methyl]-biphenyl-2-carboxylate are dissolved in 20 ml of ethanol, combined with 2 ml of 2N sodium hydroxide solution and stirred for 16 hours at ambient temperature. After the solvent has been evaporated off in vacuo the viscous residue is taken up in 50 ml of bicarbonate solution, filtered over activated charcoal and 2N acetic acid are added at 0° C. The precipitate formed is suction filtered, washed with water and dried.

Yield: 95 mg (56% of theory), Melting point: 251°–254° C. $C_{27}H_{25}ClN_6O_2$ (500.99)

Calculated: C 64.50 H 5.00 N 16.80 Cl 7.10 Found: 64.33 5.13 16.77 7.21

EXAMPLE 2

4'-[[2-n-Propyl-4-methyl-6-(2-cyano-3-methyl-guanidino)-1H-benzimidazol -1-yl]-methyl]-biphenyl-2-carboxylic acid a) Methyl 4'-[(2-n-propyl-4-methyl-6-phthalimido-1H-benzimidazol -1-yl)-methyl]biphenyl-2-carboxylate Prepared analogously to Example 1a from 2-n-propyl-4-methyl-6-phthalimido-1H-benzimidazole and methyl 4'-bromomethyl-biphenyl-2-carboxylate.

Yield: 35% of theory, Melting point: 176°–177° C.

b) Methyl 4'-[(2-n-propyl-4-methyl-6-amino-1H-benzimidazol-1-yl) -methyl]-biphenyl-2-carboxylate Prepared analogously to Example 1b from methyl 4'-[(2-n-propyl-4-methyl-6-phthalimido-1H-benzimidazol-1-yl)methyl]-biphenyl-2-carboxylate and methylamine.

Yield: 78% of theory, $R_f$ value: 0.40 (silica gel; ethyl acetate/petroleum ether =4:1)

c) Methyl 4'-[[2-n-propyl-4-methyl-6-(2-cyano-3-methyl-guanidino) -1H-benzimidazol-1-yl]-methyl]-biphenyl-2-carboxylate Prepared analogously to Example 1c from methyl 4'-[(2-n-propyl-4-methyl-6-amino-1H-benzimidazol-1-yl)-methyl]-biphenyl-2-carboxylate, diphenyl cyanocarbamidate and methylamine.

Yield: 44% of theory, Melting point: 117°–119° C.

d) 4'-[[2-n-Propyl-4-methyl-6-(2-cyano-3-methyl-guanidino) -1H-benzimidazol-1-yl]-methyl]-biphenyl-2-carboxylic acid Prepared analogously to Example 1d from methyl 4'-[[2-n-propyl-4-methyl-6-(2-cyano-3-methyl-guanidino)-1H-benzimidazol-1-yl]-methyl]-biphenyl-2-carboxylate and 2N sodium hydroxide solution in ethanol.

Yield: 40% of theory, Melting point: 247°–249° C. $C_{28}H_{28}N_6O_2$ (480.57) Mass spectrum: $M^+=480$

EXAMPLE 3

4'-[[2-n-Propyl-4-methyl-6-(2-cyano-3,3-d imethyl-guanidino) -1H-benzimidazol-1-yl]-methyl]-biphenyl-2-carboxylic acid a) Methyl 4'-[[2-n-propyl-4-methyl-6-(2-cyano-3,3-dimethyl-guanidino) -1H-benzimidazol-1-yl]-methyl]-biphenyl-2-carboxylate Prepared analogously to Example 1c from methyl 4'-[[2-n-propyl-4-methyl-6-amino-1H-benzimidazol-1-yl]-methyl]-biphenyl-2-carboxylate, diphenyl cyanocarbamidate and dimethylamine.

Yield: 34% of theory, $R_f$ value: 0.60 (silica gel; methylene chloride/ethanol=9:1)

b) 4'-[[2-n-propyl-4-methyl-6-(2-cyano-3,3-dimethyl-guanidino) -1H-benzimidazol-1-yl]-methyl]-biphenyl-2-carboxylic acid Prepared analogously to Example 1d from methyl 4'-[[2-n-propyl-4-methyl-6-(2-cyano-3,3-dimethyl-guanidino)-1H-benzimidazol-1-yl]-methyl]-biphenyl-2-carboxylate and 2N sodium hydroxide solution in ethanol.

Yield: 9.5% of theory, Melting point: sintering from 180° C. $C_{29}H_{30}N_6O_2$ (494.60) Mass spectrum: $M^+=494$

EXAMPLE 4

4'-[[2-n-Propyl-4-chloro-6-(2-cyano-3,3-dimethyl-guanidino) -1H-benzimidazol-1-yl]-methyl]-2-(1H-tetrazol-5-yl)-biphenyl a) 4'-[(2-n-Propyl-4-chloro-6-phthalimido-1H-benzimidazol-1-yl) -methyl]-2-(1-triphenylmethyl-tetrazol-5-yl)-biphenyl Prepared analogously to Example 1a from 2-n-propyl-4-chloro-6-phthalimido-1H-benzimidazole and 4'-bromomethyl-2-(1-triphenylmethyl-tetrazol-5-yl-biphenyl.

Yield: 35% of theory, $R_f$ value: 0.55 (silica gel; methylene chloride/ethanol=9:1)

b) 4'-[(2-n-propyl-4-chloro-6-amino-1H-benzimidazol-1-yl)-methyl]-2-(1-triphenylmethyl-tetrazol-5-yl)-biphenyl Prepared analogously to Example 1b from 4'-[(2-n-propyl-4-chloro-6-phthalimido-1H-benzimidazol-1-yl)-methyl] -2-(1-triphenylmethyl-tetrazol-5-yl)-biphenyl and methylamine.

Yield: 72% of theory, Melting point: 209°–210° C.

c) 4'-[[2-n-Propyl-4-chloro-6-(2-cyano-3,3-dimethyl-guanidino) -1H-benzimidazol-1-yl]-methyl]-2-(1-triphenylmethyl-tetrazol-5-yl)-biphenyl Prepared analogously to Example 1c from 4'-[(2-n-propyl-4-chloro-6-amino-1H-benzimidazol-1-yl)-methyl]-2-(1-triphenylmethyl-tetrazol-5-yl)-biphenyl, diphenyl cyanocarbamidate and dimethylamine.

Yield: 50% of theory, Melting point: sintering from 134° C.

This produces 18% of 4'-[[2-n-propyl-4-chloro-6-(2-cyano-3,3-dimethyl-guanidino) -1H-benzimidazol-1-yl]methyl]-2-(1H-tetrazol-5-yl)-biphenyl d) 4'-[[2-n-Propyl-4-chloro-6-(2-cyano-3,3-dimethyl-guanidino) -1H-benzimidazol-1-yl]-methyl]-2-(1H-tetrazol-5-yl)-biphenyl 225 mg (0.29 mMol) of 4'-[[2-n-propyl-4-chloro-6-(2-cyano-3,3-dimethyl-guanidino)-1H-benzimidazol-1-yl]methyl]-2-(1-triphenylmethyl-tetrazol-5-yl)-biphenyl are dissolved in 10 ml of absolute ethanol, mixed with 2.5 ml of methanolic hydrochloric acid and stirred for 90 minutes at ambient temperature. The solvent is then removed in vacuo and the residue is taken up in methylene chloride/ethanol (4:1) and adjusted to pH 8 with methanolic ammonia. After the addition of 5 g of silica gel the mixture is evaporated to dryness. The residue is chromatographed on silica gel (particle size: 0.032–0.063 mm) using as eluant first methylene chloride and then methylene chloride/ethanol (50:1, 25:1, 19:1 and 9:1). The uniform fractions are combined and evaporated down.

Yield: 15 mg (10% of theory), Melting point: 204°–206° C. $C_{28}H_{27}ClN_{10}$ (539.05) Mass spectrum: $(M+H)^+=539/541$ (Cl)

EXAMPLE 5

4'-[[2-n-propyl-4-chloro-6-(2-cyano-3-methyl-guanidino)-1H-benzimidazol-1-yl]-methyl]-2-(1H-tetrazol-5-yl)biphenyl a) 4'-[[2-n-Propyl-4-chloro-6-(2-cyano-3-methyl-guanidino) -1H-benzimidazol-1-yl]-methyl]-2-(1-triphenylmethyl-tetrazol-5-yl)-biphenyl Prepared analogously to Example 1c from 4'-[(2-n-propyl-4-chloro-6-amino-1H-benzimidazol-1-yl)-methyl]-2-(1-triphenylmethyl-tetrazol-5-yl)-biphenyl, diphenyl cyanocarbamidate and methylamine.

Yield: 32% of theory, Melting point: 222°–224° C.

b) 4'-[[2-n-Propyl-4-chloro-6-(2-cyano-3-methyl-guanidino) -1H-benzimidazol-1-yl]-methyl]-2-(1H-tetrazol-5-yl)-biphenyl Prepared analogously to Example 4d from 4'-[(2-n-propyl-4-chloro-6-(2-cyano-3-methyl-guanidino)-1H-benzimidazol-1-yl]-methyl]-2-(1-triphenylmethyl-tetrazol-5-yl)biphenyl and methanolic hydrochloric acid.

Yield: 11% of theory, Melting point: >250° C. $C_{27}H_{25}ClN_{10}$ (525.02) Mass spectrum: $(M+H)^+=525/527$ (Cl)

EXAMPLE 6

4'-[[2-n-propyl-4-methyl-6-(2-cyano-3-cyclohexyl-guanidino) -1H-benzimidazol-1-yl]-methyl]-2-(1H-tetrazol-5-yl)-biphenyl a) 4'-[(2-n-Propyl-4-methyl-6-phthalimido-1H-benzimidazol-1-yl)-methyl]-2-cyano-biphenyl Prepared analogously to Example 1a from 2-n-propyl-4-methyl-6-phthalimido-1H-benzimidazole and 4'-bromomethyl-2-cyano-biphenyl.

Yield: 49% of theory, Melting point: 243°–244° C.

b) 4'-[[2-n-Propyl-4-methyl-6-amino-1H-benzimidazol-1-yl]-methyl]-2-(1H-tetrazol-5-yl)-biphenyl 4.75 g (12.5 mMol) of 4'-[(2-n-propyl-4-methyl-6-phthalimido-1H-benzimidazol-1-yl)-methyl]-2-cyanobiphenyl are dissolved in 200 ml of absolute toluene and combined with 20.8 g (62.5 mMol) of tributyl tin azide. The reaction mixture is refluxed for 5 days with stirring. Then the solvent is distilled off, the residue is taken up in saline solution and extracted 3 times with 100 ml of ethyl acetate. The combined organic phases are dried over sodium sulphate and evaporated down. The residue is chromatographed on silica gel (particule size: 0.032–0.063 mm) using as eluant first methylene chloride and then methylene chloride/ethanol (50:1, 25:1 and 9:1). The uniform fractions are combined and evaporated down. The residue is triturated with ether/petroleum ether (1:1) and suction filtered.

Yield: 4.05 g (77% of theory), Melting point: sintering from 177° C.

c) 4'-[[2-n-Phenyl-4-methyl-6-(2-phenoxy-3-cyano-isoureido) -1H-benzimidazol-1-yl]-2-(1H-tetrazol-5-yl)-biphenyl 1.70 g (4.0 mMol) of 4'-[[2-n-propyl-4-methyl-6-amino-1H-benzimidazol-1-yl]-methyl]-2-(1H-tetrazol-5-yl)biphenyl are taken up in 150 ml of isopropanol and mixed with 30 ml of methylene chloride and 3.1 g (13 mMol) of diphenyl cyanocarbamidate. The reaction solution is stirred at ambient temperature for 3 days and then evaporated down. The residue is chromatographed on silica gel (particule size: 0.032–0.063 mm), using as eluant first methylene chloride and then methylene chloride/ethanol (50:1, 25:1 and 9:1). The uniform fractions are combined and evaporated down. The residue is triturated with ether/petroleum ether (1:1) and suction filtered.

Yield: 905 mg (40% of theory), Melting point: >250° C.

d) 4'-[[2-n-Propyl-4-methyl-6-(2-cyano-3-cyclohexyl-guanidino) -1H-benzimidazol-1-yl]-methyl]-2-(1H-tetrazol-5-yl)-biphenyl Prepared analogously to Example 1c from 4'-[[2-n-propyl-4-methyl-6-(2-phenoxy-3-cyano-isoureido)-1H-benzimidazol-1-yl] -methyl]-2-(1H-tetrazol-5-yl)-biphenyl and cyclohexylamine in boiling isopropanol.

Yield: 44% of theory, Melting point: sintering from 188° C. $C_{33}H_{36}N_{10}$ (572.72) Mass spectrum: $(M+H)^+=573$

EXAMPLE 7

4'-[[2-n-Propyl-4-methyl-6-(2-cyano-3,3-dimethyl-guanidino) -1H-benzimidazol-1-yl]-methyl]-2-(1H-tetrazol-5-yl)-biphenyl Prepared analogously to Example 1c from 4'-[[2-n-propyl-4-methyl-6-(2-phenoxy-3-cyano-isoureido)-1H-benzimidazol -1-yl]-methyl]-2-(1H-tetrazol-5-yl)-biphenyl and dimethylamine in boiling isopropanol.

Yield: 24% of theory, Melting point: sintering from 202° C. $C_{29}H_{30}N_{10}$ (518.63) Mass spectrum: $M^+=518$

EXAMPLE 8

4'-[[2-n-Propyl-4-methyl-6-(2-cyano-3-isopropyl-guanidino) -1H-benzimidazol-1-yl]-methyl]-2-(1H-tetrazol-5-yl)-biphenyl Prepared analogously to Example 1c from 4'-[[2-n-propyl-4-methyl-6-(2-phenoxy-3-cyano-isoureido)-1H-benzimidazol -1-yl]-methyl]-2-(1H-tetrazol-5-yl)-biphenyl and isopropylamine in boiling isopropanol.

Yield: 39% of theory, Melting point: sintering from 198° C. $C_{30}H_{32}N_{10}$ (532.66) Mass spectrum: $M^+=532$

EXAMPLE 9

4'-[[2-n-Propyl-4-methyl-6-(2-cyano-3,3-diisopropyl-guanidino) -1H-benzimidazol-1-yl]-methyl]-2-(1H-tetrazol-5-yl)-biphenyl Prepared analogously to Example 1c from 4'-[[2-n-propyl-4-methyl-6-(2-phenoxy-3-cyano-isoureido)-1H-benzimidazol -1-yl]-methyl]-2-(1H-tetrazol-5-yl)-biphenyl and diisopropylamine in boiling isopropanol.

Yield: 19% of theory, Melting point: sintering from 185° C. $C_{33}H_{38}N_{10}$ (574.74)

Mass spectrum: $(M+H)^+=575$

EXAMPLE 10

4'-[[2-n-Propyl-4-methyl-6-(2,2-dicyano-1-pyrrolidino-etheneamino)-1H-benzimidazol-1-yl]-methyl]-biphenyl-2-carboxylic acid a) Tert.butyl 4'-[(2-n-propyl-4-methyl-6-phthalimido-1H-benzimidazol-1-yl)-methyl]-biphenyl-2-carboxylic acid Prepared analogously to Example 1a from 2-n-propyl-4-methyl-6-phthalimido-1H-benzimidazole and tert.butyl 4'-bromomethyl-biphenyl-2-carboxylate.

Yield: 68% of theory, Melting point: 153°–154° C.

b) Tert.butyl 4'-[(2-n-propyl-4-methyl-6-amino-1H-benzimidazol-1-yl)-methyl]-biphenyl-2-carboxylate Prepared analogously to Example 1b from tert.butyl 4'-[(2-n-propyl-4-methyl-6-phthalimido-1H-benzimidazol-1-yl)-methyl]-biphenyl-2-carboxylate and methylamine.

Yield: 94% of theory, Melting point: 118°–119° C.

c) Tert.butyl 4'-[[2-n-propyl-4-methyl-6-(2,2-dicyano-1-methylmercapto-etheneamino)-1H-benzimidazol-1-yl]-methyl]-biphenyl-2-carboxylate 2.70 ml (6.1 mMol) of tert.butyl 4'-[[2-n-propyl-4-methyl-6-amino-1H-benzimidazol-1-yl]-methyl]-biphenyl-2-carboxylate are dissolved in 125 ml of isopropanol, mixed with 2.38 g (14 mMol) of 2,2-dicyano-1,1-dimethylmercapto-ethene and refluxed for 4 days. The solvent is evaporated off, the residue is chromatographed on silica gel (particle size: 0.032–0.063 mm), using as eluant first methylene chloride and then methylene chloride/ethanol (50:1 and 25:1). The uniform fractions are combined and evaporated down. The residue is triturated with ether and suction filtered.

Yield: 2.15 g (62% of theory), Melting point: 186°–188° C.

d) Tert.butyl 4'-[[2-n-propyl-4-methyl-6-(2,2-dicyano-1-pyrrolidino-etheneamino)-1H-benzimidazol-1-yl]methyl]-biphenyl-2-carboxylate 425 mg (0.75 mMol) of tert.butyl 4'-[[2-n-propyl-4-methyl-6-(2,2-dicyano-1-methylmercapto-etheneamino)-1H-benzimidazol-1-yl]-methyl]-biphenyl-2-carboxylate are dissolved in 25 ml of methylene chloride. Then at 0° C. under nitrogen a solution of 380 mg (1.1 mMol) of 50% 3-chloro-peroxybenzoic acid in 5 ml of methylene chloride is added dropwise. The solution is stirred for 5 hours at ambient temperature, then 1.17 g (16.5 mMol) of pyrrolidine are added and the mixture is stirred for a further 12 hours at ambient temperature. Then the solvent is evaporated off, the residue is chromatographed on silica gel (particle size: 0.032–0.063 mm), using as eluant first methylene chloride and then methylene chloride/ethanol (50:1, 25:1 and 19:1). The uniform fractions are combined and evaporated down.

Yield: 185 mg (41% of theory), $R_f$ value: 0.40 (silica gel; methylene chloride/ethanol=19:1)

e) 4'-[[2-n-Propyl-4-methyl-6-(2,2-dicyano-1-pyrrolidino-etheneamino)-1H-benzimidazol-1-yl]methyl]-biphenyl-2-carboxylic acid 185 mg (0.31 mMol) of tert.butyl 4'-[[2-n-propyl-4-methyl-6-(2,2-dicyano-1-pyrrolidino-etheneamino)-1H-benzimidazol-1-yl]-methyl]-biphenyl-2-carboxylate are dissolved in 10 ml of methylene chloride and mixed with 1.5 ml of trifluoroacetic acid. After 3 hours at ambient temperature, the solution is evaporated down, the residue is taken up in 25 ml of sodium bicarbonate solution and filtered over activated charcoal. The precipitate formed after the addition of 2N acetic acid at 5° C. is suction filtered and dried.

Yield: 37 mg (22% of theory), Melting point: 188°–190° C. $C_{33}H_{32}N_6O_2$ (544.66) Mass spectrum: $(M+H)^+=545$

EXAMPLE 11

4'-[[2-n-Propyl-4-methyl-6-(2,2-dicyano-1-methylamino-etheneamino)-1H-benzimidazol-1-yl]-methyl]-biphenyl-2-carboxylic acid a) Tert.butyl 4'-[[2-n-propyl-4-methyl-6-(2,2-dicyano-1-methylamino-etheneamino)-1H-benzimidazol-1-yl]methyl]-biphenyl-2-carboxylate Prepared analogously to Example 10d from tert.butyl 4'-[(2-n-propyl-4-methyl-6-(2,2-dicyano-1-methylmercapto-etheneamino)-1H-benzimidazol-1-yl)-methyl]-biphenyl-2-carboxylate, 3-chloro-peroxybenzoic acid and methylamine.

Yield: 44% of theory, Melting point: 240°–242° C.

b) 4'-[[2-n-Propyl-4-methyl-6-(2,2-dicyano-1-methylamino-etheneamino)-1H-benzimidazol-1-yl]methyl]-biphenyl-2-carboxylic acid Prepared analogously to Example 10e from tert.butyl 4'-[[2-n-propyl-4-methyl-6-(2,2-dicyano-1-methylamino-etheneamino)-1H-benzimidazol-1-yl]-methyl]-biphenyl-2-carboxylate and trifluoroacetic acid.

Yield: 43% of theory, Melting point: sintering from 178° C. $C_{30}H_{28}N_6O_2$ (504.60) Mass spectrum: $M^+=504$

EXAMPLE 12

4'-[[2-n-Propyl-4-methyl-6-(2,2-dicyano-1-dimethylamino-etheneamino)-1H-benzimidazol-1-yl]-methyl]-biphenyl-2-carboxylic acid a) Tert.butyl 4'-[[2-n-propyl-4-methyl-6-(2,2-dicyano-1-dimethylamino-etheneamino)-1H-benzimidazol-1-yl]methyl]-biphenyl-2-carboxylate Prepared analogously to Example 10d from tert.butyl 4'[[2-n-propyl-4-methyl-6-(2,2-dicyano-1-methylmercapto-etheneamino)-1H-benzimidazol-1-yl]-methyl]-biphenyl-2-carboxylate and dimethylamine.

Yield: 38% of theory, Melting point: sintering from 138° C.

b) 4'-[[2-n-Propyl-4-methyl-6-(2,2-dicyano-1-dimethylamino-etheneamino)-1H-benzimidazol-1-yl]methyl]-biphenyl-2-carboxylic acid Prepared analogously to Example 10e from tert.butyl 4'[[2-n-propyl-4-methyl-6-(2,2-dicyano-1-dimethylamino-etheneamino)-1H-benzimidazol-1-yl]-methyl]-biphenyl-2-carboxylate and trifluoroacetic acid.

Yield: 49% of theory, Melting point: 178° C. $C_{31}H_{30}N_6O_2$ (518.62) Mass spectrum: $M^+=519$

EXAMPLE 13

4'-[[2-n-Propyl-4-methyl-6-(2,2-dicyano-1-dimethylamino-etheneamino)-1H-benzimidazol-1-yl]-methyl]-2-(1H-tetrazol-5-yl)-biphenyl a) 4'-[[2-n-Propyl-4-methyl-6-(2,2-dicyano-1-methylmercapto-etheneamino)-1H-benzimidazol-1-yl]-methyl]-(1H-tetrazol-5-yl)-biphenyl Prepared analogously to Example 10c from 4'-[[2-n-propyl-4-methyl-6-amino-1H-benzimidazol-1-yl]-methyl]-2-(1H-tetrazol-5-yl)-biphenyl and 2,2-dicyano-1,1-dimethylmercapto-ethene.

Yield: 79% of theory, Melting point: 184°–185° C.

b)   4'-[[2-n-Propyl-4-methyl-6-(2,2-dicyano-1-dimethylamino-etheneamino) -1H-benzimidazol-1-yl]methyl]-2-(1H-tetrazol-5-yl)-biphenyl Prepared analogously to Example 10d from 4'-[[2-n-propyl-4-methyl-6-(2,2-dicyano-1-methylmercapto-etheneamino) -1H-benzimidazol-1-yl]-methyl]-2-(1H-tetrazol-5-yl)-biphenyl and dimethylamine.

Yield: 29% of theory, Melting point: sintering from 208° C. $C_{31}H_{30}N_{10}$ (542.65) Mass spectrum: $(M+H)^+=543$

EXAMPLE 14

4'-[[2-n-Propyl-4-methyl-6-(1-dimethylamino-2-nitro-etheneamino)
-1H-benzimidazol-1-yl]-methyl]-biphenyl-2-carboxylic acid a) Methyl 4'-[[2-n-propyl-4-methyl-6-(1-methylmercapto-2-nitro-etheneamino) -1H-benzimidazol-1-yl]methyl]-biphenyl-2-carboxylate 826 mg (2.0 mMol) of methyl 4'-[(2-n-propyl-4-methyl-6-amino-1H-benzimidazol -1-yl)-methyl]-biphenyl-2-carboxylate are dissolved in 75 ml of isopropanol, mixed with 0.97 g (6.0 mMol) of 1,1-bis-(methylmercapto)-2-nitroethene and refluxed for 6 hours. Then the solvent is evaporated off, the residue is recrystallised from isopropanol/petroleum ether (3:1) with the addition of activated charcoal.

Yield: 745 mg (70% of theory), Melting point: 173°–174° C.

b) Methyl 4'-[[2-n-propyl-4-methyl-6-(1-dimethylamino-2-nitro-etheneamino) -1H-benzimidazol-1-yl]-methyl]-biphenyl-2-carboxylate 250 mg (0.47 mMol) of methyl 4'-[(2-n-propyl-4-methyl-6-(1-methylmercapto-2-nitro-etheneamino)-1H-benzimidazol -1-yl)-methyl]-biphenyl-2-carboxylate are dissolved in 50 ml of isopropanol, mixed with 1.0 ml of dimethylamine and heated to 60° C. for 3 hours in a pressurised vessel. After cooling to ambient temperature the precipitate formed is filtered off, washed with water and ether and dried.

Yield: 195 mg (79% of theory), Melting point: 127°–128° C.

c)   4'-[[2-n-propyl-4-methyl-6-(1-dimethylamino-2-nitro-etheneamino) -1H-benzimidazol-1-yl]-methyl]-biphenyl-2-carboxylic acid Prepared analogously to Example 1d from methyl 4'-[[2-n-propyl-4-methyl-6-(1-dimethylamino-2-nitro-etheneamino) -1H-benzimidazol-1-yl]-methyl]-biphenyl-2-carboxylate and 2N sodium hydroxide solution in ethanol.

Yield: 34% of theory, Melting point: sintering from 200° C. $C_{29}H_{31}N_5O_4$ (513.60) Mass spectrum: $M^+=513$

EXAMPLE 15

4'-[[2-n-Propyl-4-methyl-6-(1-methylamino-2-nitro-etheneamino)
-1H-benzimidazol-1-yl]-methyl]-biphenyl-2-carboxylic acid a) Methyl 4'-[[2-n-propyl-4-methyl-6-(1-methylamino-2-nitro-etheneamino) -1H-benzimidazol-1-yl]-methyl]-biphenyl-2-carboxylate Prepared analogously to Example 14b from methyl 4'-[[2-n-propyl-4-methyl-6-(1-methylmercapto-2-nitro-etheneamino) -1H-benzimidazol-1-yl]-methyl]-biphenyl-2-carboxylate and methylamine.

Yield: 68% of theory, $R_f$ value: 0.15 (silica gel; methylene chloride/ethanol=9:1)

b) 4'-[[2-n-propyl-4-methyl-6-(1-methylamino-2-nitro-etheneamino) -1H-benzimidazol-1-yl]-methyl]-biphenyl-2-carboxylic acid Prepared analogously to Example 1d from methyl 4'-[[2-n-propyl-4-methyl-6-(1-methylamino-2-nitro-etheneamino) -1H-benzimidazol-1-yl]-methyl]-biphenyl-2-carboxylate and 2N sodium hydroxide solution in ethanol.

Yield: 30% of theory, Melting point: sintering from 188° C. $C_{28}H_{29}N_5O_4$ (499.57) Mass spectrum: $M^+=499$

EXAMPLE 16

4'-[[2-n-Propyl-4-methyl-6-(3-methyl-2-amidosulphonyl-guanidino)
-1H-benzimidazol-1-yl]-methyl]-biphenyl-2-carboxylic acid a)   Methyl 4'-[[2-n-propyl-4-methyl-6-(3-methyl-2-amidosulphonyl-guanidino) -1H-benzimidazol-1-yl]methyl]-biphenyl-2-carboxylate 413 mg (1.0 mMol) of methyl 4'-[(2-n-propyl-4-methyl-6-amino-1H-benzimidazol -1-yl)-methyl]-biphenyl-2-carboxylate are dissolved in 50 ml of isopropanol, mixed with 1.17 g (4.0 mMol) of diphenyl amidosulphonylcarbamidate and stirred for 2 days at ambient temperature. After the addition of 1.5 ml of methylamine the reaction mixture is heated to 60° C. for 3 hours in a pressurised vessel. Then the solvent is evaporated off, the residue is chromatographed on silica gel (particle size: 0.032–0.063 mm), using as eluant first methylene chloride and then methylene chloride/ethanol (50:1, 25:1 and 19:1). The uniform fractions are combined and evaporated down, the residue is triturated from ether/petroleum ether (1:1) and suction filtered.

Yield: 235 mg (43% of theory), Melting point: 115°–117° C.

b) 4'-[[2-n-propyl-4-methyl-6-(3-methyl-2-amidosulphonyl-guanidino) -1H-benzimidazol-1-yl]-methyl]-biphenyl-2-carboxylic acid Prepared analogously to Example 1d from methyl 4'-[[2-n-propyl-4-methyl-6-(3-methyl-2-amidosulphonyl-guanidino)-1H -benzimidazol-1-yl]-methyl]-biphenyl-2-carboxylate and 2N sodium hydroxide solution in ethanol.

Yield: 31% of theory, Melting point: 208° C. $C_{27}H_{30}N_6O_4S$ (534.64) Mass spectrum: $(M+H)^+=535$

EXAMPLE 17

4'-[[2-n-Propyl-4-methyl-6-(3,3-dimethyl-2-amidosulphonyl-guanidino)
-1H-benzimidazol-1-yl]-methyl]-biphenyl-2-carboxylic acid a) Methyl 4'-[[2-n-propyl-4-methyl-6-(3,3-dimethyl-2-amidosulphonyl-guanidino) -1H-benzimidazol-1-yl]methyl]-biphenyl-2-carboxylate Prepared analogously to Example 16a from methyl 4'-[(2-n-propyl-4-methyl-6-amino-1H-benzimidazol-1-yl)-methyl]-biphenyl-2-carboxylate, diphenyl amidosulphonylcarbamidate and dimethylamine.

Yield: 56% of theory, Melting point: 188°–189° C.

b)   4'-[[2-n-Propyl-4-methyl-6-(3,3-dimethyl-2-amidosulphonyl-guanidino) -1H-benzimidazol-1-yl]methyl]-biphenyl-2-carboxylic acid Prepared analogously to Example 1d from methyl 4'-[[2-n-propyl-4-methyl-6-(3,3-dimethyl-2-amidosulphonyl-guanidino) -1H-benzimidazol-1-yl]-methyl]-biphenyl-2-carboxylate and 2N sodium hydroxide solution in ethanol.

Yield: 26% of theory, Melting point: sintering from 165° C. $C_{28}H_{32}N_6O_4S$ (548.67) Mass spectrum: $(M+H)^+=549$

EXAMPLE 18

4'-[[2-n-Propyl-4-methyl-6-[2-cyano-3-(2-dimethylamino-ethyl)-3-methyl-guanidino]-1H-benzimidazol-1-yl]methyl]-2-(1H-tetrazol-5-yl)-biphenyl Prepared analogously to Example 6d from 4'-[[2-n-propyl-4-methyl-6-(2-phenoxy-3-cyano-isoureido)-1H-benzimidazol -1-yl]-methyl]-2-(1H-tetrazol-5-yl)-biphenyl and N-(2-dimethylamino-ethyl)-methylamine in isopropanol.

Yield: 40% of theory, Melting point: 220° C. (sintering from 115° C.) $C_{32}H_{37}N_{11}$ (575.74) Mass spectrum: $(M+H)^+=576$

EXAMPLE 19

4'-[[2-n-Propyl-4-methyl-6-[2-cyano-3-(2-hydroxy-ethyl)-3-methyl-guanidino]-1H-benzimidazol-1-yl]-methyl]-2-(1H-tetrazol-5-yl)-biphenyl Prepared analogously to Example 6d from 4'-[[2-n-propyl-4-methyl-6-(2-phenoxy-3-cyano-isoureido)-1H-benzimidazol-1-yl]-methyl]-2-(1H-tetrazol-5-yl)-biphenyl and N-(2-hydroxy-ethyl)-methylamine in isopropanol.

Yield: 47.5% of theory, Melting point: 230° C. (sintering from 108° C.) $C_{30}H_{32}N_{10}O$ (548.67) Mass spectrum: $(M+H)^+=549$

EXAMPLE 20

4'-[[2-n-Propyl-4-methyl-6-[2-cyano-3-(bis-2-methoxy-ethyl)-guanidino]-1H-benzimidazol-1-yl]methyl]-2-(1H-tetrazol-5-yl)-biphenyl Prepared analogously to Example 6d from 4'-[[2-n-propyl-4-methyl-6-(2-phenoxy-3-cyano-isoureido)-1H-benzimidazol-1-yl]-methyl]-2-(1H-tetrazol-5-yl)-biphenyl and bis-(2-methoxy)-ethylamine in isopropanol.

Yield: 27.5% of theory, Melting point: 104°–106° C. (sintering from 70° C.) $C_{33}H_{38}N_{10}O_2$ (606.74) Mass spectrum: $M^+=606$

EXAMPLE 21

4'-[[2-n-Propyl-4-methyl-6-(N-(2-methyl-1-cyanimino-propyl)-amino) -1H-benzimidazol-1-yl]-methyl]-2-(1H-tetrazol-5-yl)-biphenyl a) (1-Methyl-ethyl)-(methylmercapto)-methyleneiminonitrile A Grignard solution prepared from 28.0 g (0.23 mol) of isopropylbromide and 5.5 g (0.23 mol) of magnesium in 10 ml of diethylether is added dropwise within 30 minutes, whilst cooling with ice, to a solution of 22.0 g (0.15 mol) of dimethylcyanoimidodithiocarbonate in 150 ml of tetrahydrofuran. The solution is stirred for 24 hours at ambient temperature and then mixed with 100 ml of 4N hydrochloric acid. After phase separation, the aqueous phase is extracted 3 times with 50 ml of ethyl acetate. The combined organic phases are washed with saline solution and dried with sodium sulphate. The crude product is chromatographed on silica gel (particle size: 0.032–0.063 mm) using first petroleum ether and then mixtures of petroleum ether/ethyl acetate (19:1, 9:1 and 4:1). The uniform fractions are combined and evaporated down.

Yield: 4.65 g (22% of theory), $R_f$ value: 0.40 (silica gel; petroleum ether/ethyl acetate =9:1)

b) 4'-[[2-n-Propyl-4-methyl-6-(N-(2-methyl-1-cyanimino-propyl)-amino) -1H-benzimidazol-1-yl]-methyl]-2-(1H-tetrazol-5-yl)-biphenyl Prepared analogously to Example 1c from 4'-[(2-n-propyl-4-methyl-6-amino-1H-benzimidazol-1-yl)-methyl]-2-(1H-tetrazol -5-yl)-biphenyl and (1-methyl-ethyl)-(methylmercapto)-methylene-imino-nitrile in isopropanol.

Yield: 20.3% of theory, Melting point: 208°–210° C. (sintering from 162° C.), $C_{30}H_{31}N_9$ (517.65) Mass spectrum: $M^+=517$

EXAMPLE 22

4'-[[2-n-Propyl-4-methyl-6-[2-cyano-3-(2-hydroxy-ethyl)-3-methyl-guanidino]-1H-benzimidazol-1-yl]-methyl]-biphenyl-2-carboxylic acid Prepared analogously to Example 1d from methyl 4'-[[2-n-propyl-4-methyl-6-[2-cyano-3-(2-hydroxy-ethyl)-3-methylguanidino]-1H-benzimidazol-1-yl]-methyl]-biphenyl-2-carboxylate and 2N sodium hydroxide solution in ethanol.

Yield: 9.5% of theory, Melting point: 212° C. (sintering from 190° C.), $C_{30}H_{32}N_6O_3$ (524.64) Mass spectrum: $(M-H)^-=523$

EXAMPLE 23

4'-[[2-n-Propyl-4-methyl-6-[2-cyano-3,3-[bis(2-diethylaminoethyl)]-guanidino]-1H-benzimidazol-1-yl]methyl]-biphenyl-2-carboxylic acid Prepared analogously to Example 1d from methyl 4'-[[2-n-propyl-4-methyl-6-[2-cyano-3,3-[bis(2-diethylaminoethyl)]-guanidino]-1H-benzimidazol-1-yl]-methyl]-biphenyl-2-carboxylate and 2N sodium hydroxide solution in ethanol.

Yield: 28.8% of theory, Melting point: 168° C. (sintering from 112° C.), $C_{39}H_{51}N_8O_2$ (663.89) Mass spectrum: $(M-H)^-=663$

EXAMPLE 24

4'-[[2-Ethyl-4-methyl-6-[3-cyano-2-(4-methyl-piperazino)-amidino]-1H-benzimidazol-1-yl]-methyl]-biphenyl-2-carboxylic acid Prepared analogously to Example 1d from methyl 4'-[[2-ethyl-4-methyl-6-[3-cyano-2-(4-methyl-piperazino)amidino]-1H-benzimidazol-1-yl]-methyl]-biphenyl-2-carboxylate and 2N sodium hydroxide solution in ethanol.

Yield: 3.9% of theory, Melting point: 218° C. (sintering from 173° C.), $C_{31}H_{33}N_7O_2$ (535.66) Mass spectrum: $(M+H)^+=536$

EXAMPLE 25

4'-[[2-Ethyl-4-methyl-6-(2-cyano-3,3-dimethyl-guanidino) -1H-benzimidazol-1-yl]-methyl]-2-(1H-tetrazol-5-yl)-biphenyl Prepared analogously to Example 6d from 4'-[[2-ethyl-4-methyl-6-(2-phenoxy-3-cyano-isoureido)-1H-benzimidazol-1-yl]-methyl]-2-(1H-tetrazol-5-yl)-biphenyl and dimethylamine in isopropanol.

Yield: 17.8% of theory, Melting point: sintering from 202° C. $C_{28}H_{28}N_{10}$ (504.61) Mass spectrum: $M^+=504$

EXAMPLE 26

4'-[[2-Ethyl-4-methyl-6-(2-cyano-3,3-dimethyl-guanidino)
-1H-benzimidazol-1-yl]-methyl]-biphenyl-2-carboxylic
acid Prepared analogously to Example 1d from methyl 4'-[[2-ethyl-4-methyl-6-(2-cyano-3,3-dimethyl-guanidino)-1H-benzimidazol -1-yl]-methyl]-biphenyl-2-carboxylate and 2N sodium hydroxide solution in ethanol.

Yield: 25.0% of theory, Melting point: 208°–210° C. (sintering from 176° C.) $C_{28}H_{28}N_6O_2$ (480.58) Mass spectrum: $M^+=480$

EXAMPLE 27

4'-[[2-Propyl-4-methyl-6-[1-(N-(2-dimethylamino-ethyl)-methylamino)
-2-nitro-ethyleneamino]-1H-benzimidazol-1-yl]-methyl]-biphenyl-2-carboxylic acid Prepared analogously to Example 1d from methyl 4'-[[2-n-propyl-4-methyl-6-[1-(N-(2-dimethylamino-ethyl)-methylamino) -2-nitro-ethyleneamino]-1H-benzimidazol-1-yl] -methyl]-biphenyl-2-carboxylate and 2N sodium hydroxide solution in ethanol.

Yield: 25.0% of theory, Melting point: 218° C. (sintering from 202° C.) $C_{32}H_{38}N_6O_4$ (570.70) Mass spectrum: $(M-H)^-=569$

EXAMPLE 28

4'-[[2-n-Propyl-4-methyl-6-(1,1-dimethylamino-2-nitro-etheneamino)
-1H-benzimidazol-1-yl]-methyl]-2-(1H-tetrazol-5-yl)-biphenyl Prepared analogously to Example 14b from 4'-[(2-n-propyl-4-methyl-6-(1-methylmercapto-2-nitro-etheneamino) -1H-benzimidazol-1-yl)-methyl]-2-(1H-tetrazol-5-yl)-biphenyl and dimethylamine.

Yield: 9.5% of theory, Melting point: sintering from 172° C. $C_{29}H_{31}N_9O_2$ (537.64) Mass spectrum: $(M+H)^+=538$

EXAMPLE 29

4'-[[2-Ethyl-4-methyl-6-(1,1-dimethylamino-2-nitro-etheneamino)
-1H-benzimidazol-1-yl]-methyl]-2-(1H-tetrazol-5-yl)-biphenyl Prepared analogously to Example 14b from 4'-[(2-ethyl-4-methyl-6-(1-methylmercapto-2-nitro-etheneamino)-1H-benzimidazol-1-yl) -methyl]-2-(1H-tetrazol-5-yl)-biphenyl and dimethylamine.

Yield: 23.1% of theory, Melting point: sintering from 196° C. $C_{28}H_{29}N_9O_2$ (523.61) Mass spectrum: $(M+H)^+=524$

EXAMPLE 30

4'-[[2-n-Propyl-4-methyl-6-(1-morpholino-2-nitro-etheneamino)
-1H-benzimidazol-1-yl]-methyl]-2-(1H-tetrazol-5-yl)-biphenyl Prepared analogously to Example 14b from 4'-[[2-n-propyl-4-methyl-6-(1-methylmercapto-2-nitro-etheneamino) -1H-benzimidazol-1-yl]-2-(1H-tetrazol-5-yl)-biphenyl and morpholine.

Yield: 9.2% of theory, Melting point: 178° C. (sintering from 118° C.) $C_{31}H_{33}N_9O_3$ (579.67) Mass spectrum: $(M+H)^+=580$

EXAMPLE 31

4'-[[2-n-Propyl-4-methyl-6-[1-(N-(2-dimethylamino-ethyl)-methylamino)
-2-nitro-etheneamino]-1H-benzimidazol-1-yl]-methyl]-2-(1H-tetrazol-5-yl)-biphenyl Prepared analogously to Example 14b from 4'-[[2-n-propyl-4-methyl-6-(1-methylmercapto-2-nitro-etheneamino) -1H-benzimidazol-1-yl]-methyl]-2-(1H-tetrazol-5-yl)-biphenyl and 2-dimethylamino-methylamine.

Yield: 9.2% of theory, Melting point: 182° C. (sintering from 145° C.) $C_{32}H_{38}N_{10}O_2$ (594.73) Mass spectrum: $(M+H)^+=595$

EXAMPLE 32

4'-[[2-Ethyl-4-methyl-6-[(2-dimethylamino-3,4-dioxo-1-cyclobuten-1-yl)
-amino]-1H-benzimidazol-1-yl]-methyl]-biphenyl-2-carboxylic acid a) Methyl 4'-[[2-ethyl-4-methyl-6-[(2-dimethylamino-3,4-dioxo-1-cyclobuten-1-yl) -amino]-1H-benzimidazol-1-yl]methyl]-biphenyl-2-carboxylate Prepared analogously to Example 1c from methyl 4'-[[2-ethyl-4-methyl-6-amino-1H-benzimidazol-1-yl]-methyl]-biphenyl-2-carboxylate, 3,4-diethoxy-3-cyclobuten-1,2-dione and dimethylamine in isopropanol.

Yield: 74% of theory, Resin, $R_f$ value: 0.40 (silica gel, methylene chloride/methanol=9:1)

b) 4'-[[2-Ethyl-4-methyl-6-[(2-dimethylamino-3,4-dioxo-1-cyclobuten-1-yl) -amino]-1H-benzimidazol-1-yl]-methyl]-biphenyl-2-carboxylic acid Prepared analogously to Example 1d from methyl 4'-[[2-ethyl-4-methyl-6-[(2-dimethylamino-3,4-dioxo-1-cyclobuten-1-yl) -amino]-1H-benzimidazol-1-yl]-methyl]-biphenyl-2-carboxylate and 1N sodium hydroxide solution in ethanol.

Yield: 26.5% of theory, Melting point: 312°–315° C. $C_{30}H_{28}N_4O_4$ (508.60) Mass spectrum: $M^+=508$

EXAMPLE 33

4'-[[2-Ethyl-4-methyl-6-[(2-dimethylamino-3,4-dioxo-1-cyclobuten-1-yl)
-amino]-1H-benzimidazol-1-yl]-methyl]-2-(1H-tetrazol-5-yl)-biphenyl Prepared analogously to Example 14b from 4'-[[2-ethyl-4-methyl-6-[(2-ethoxy-3,4-dioxo-1-cyclobuten-1-yl)-amino]-1H -benzimidazol-1-yl]-methyl]-2-(1H-tetrazol-5-yl)biphenyl and dimethylamine.

Yield: 38.8% of theory, Melting point: 286°–290° C. $C_{30}H_{28}N_8O_2$ (532.61) Mass spectrum: $(M+H)^+=533$

EXAMPLE 34

4'-[[2-Ethyl-4-methyl-6-(3,3-dimethyl-2-methylsulphonyl-guanidino)-1H-benzimidazol-1-yl]-methyl]-biphenyl-2-carboxylic acid Prepared analogously to Example 1d from methyl 4'-[[2-ethyl-4-methyl-6-(3,3-dimethyl-2-methylsulphonyl-guanidino)-1H-benzimidazol-1-yl]-methyl]-biphenyl-2-carboxylate and 2N sodium hydroxide solution in ethanol.

Yield: 47.9% of theory, Melting point: 204°–206° C. $C_{28}H_{31}N_5O_4S$ (533.60) Mass spectrum: $(M-H)^-=532$

EXAMPLE 35

4'-[[2-Ethyl-4-methyl-6-(3,3-dimethyl-2-methylsulphonyl-guanidino)-1H-benzimidazol-1-yl]-methyl]-2-(1H-tetrazol-5-yl)-biphenyl Prepared analogously to Example 14b from 4'-[[2-ethyl-4-methyl-6-(2-phenoxy-3-methylsulphonyl-isoureido)-1H-benzimidazol-1-yl]-methyl]-2-(1H-tetrazol-5-yl)-biphenyl and dimethylamine.

Yield: 58.0% of theory, Melting point: 197°–199° C. (sintering from 172° C.) $C_{28}H_{31}N_9O_2S$ (557.69) Mass spectrum: $(M+H)^+=558$

EXAMPLE 36

4'-[[2-Ethyl-4-methyl-6-(3,3-dimethyl-2-phenylsulphonyl-guanidino)-1H-benzimidazol-1-yl]-methyl]-biphenyl-2-carboxylic acid Prepared analogously to Example 1d from methyl 4'-[[2-ethyl-4-methyl-6-(3,3-dimethyl-2-phenylsulphonyl-guanidino)-1H-benzimidazol-1-yl]-methyl]-biphenyl-2-carboxylate and 2N sodium hydroxide solution in ethanol.

Yield: 30.8% of theory, Melting point: 218°–220° C. $C_{33}H_{33}N_5O_4S$ (595.70) Mass spectrum: $(M+H)^+=596$

EXAMPLE 37

4'-[[2-n-Propyl-4-methyl-6-[N-(3-nitro-pyrrol-2-yl)amino]-1H-benzimidazol-1-yl]-methyl]-biphenyl-2-carboxylic acid a) Methyl 4'-[[2-n-propyl-4-methyl-6-[1-(2-diethoxy-ethylamino)-2-nitro-etheneamino]-1H-benzimidazol-1-yl]-methyl]-biphenyl-2-carboxylate Prepared analogously to Example 14b from methyl 4'-[[2-n-propyl-4-methyl-6-(1-methylmercapto-2-nitro-etheneamino)-1H-benzimidazol-1-yl]-methyl]-biphenyl-2-carboxylate and aminoacetaldehyde-diethylacetal.

Yield: 32% of theory, Oil, $R_f$ value: 0.50 (silica gel; methylene chloride/ethanol=19:1)

b) Methyl 4'-[[2-n-propyl-4-methyl-6-[N-(3-nitro-pyrrol-2-yl)-amino]-1H-benzimidazol-1-yl]-methyl]-biphenyl-2-carboxylate 190 mg (0.3 mMol) of methyl 4'-[[2-n-propyl-4-methyl-6-[1-(2-diethoxy)-ethylamino-2-nitro-etheneamino]-1H-benzimidazol-1-yl]-methyl]-biphenyl-2-carboxylate are heated in 50 ml of 0.05 N hydrochloric acid over a steam bath for 30 minutes. After cooling, the pH is adjusted to pH 8 using sodium carbonate solution and the mixture is extracted 3 times with ethyl acetate. The combined organic phases are washed with saline solution and dried over sodium sulphate. After evaporation the residue obtained is chromatographed on silica gel, using methylene chloride to start with, followed by methylene chloride/ethanol 25:1 and 19:1. The uniform fractions are combined and evaporated down.

Yield: 105 mg (65% of theory), Oil, $R_f$ value: 0.50 (silica gel; methylene chloride/ethanol=19:1)

c) 4'-[[2-n-Propyl-4-methyl-6-[N-(3-nitro-pyrrol-2-yl)amino]-1H-benzimidazol-1-yl]-methyl]-biphenyl-2-carboxylic acid Prepared analogously to Example 1d from methyl 4'-[[2-n-propyl-4-methyl-6-[N-(3-nitro-pyrrol-2-yl)-amino]-1H-benzimidazol-1-yl]-methyl]-biphenyl-2-carboxylate and 2N sodium hydroxide solution in ethanol.

Yield: 16.9% of theory, Melting point: sintering from 165° C. $C_{29}H_{27}N_5O_4$ (509.60) Mass spectrum: $(M-H)^-=508$

EXAMPLE 38

4'-[[2-Ethyl-4-methyl-6-(3,3-dimethyl-2-cyano-1-methyl-guanidino)-1H-benzimidazol-1-yl]-methyl]-biphenyl-2-carboxylic acid Prepared analogously to Example 1d from methyl 4'-[[2-ethyl-4-methyl-6-(3,3-dimethyl-2-cyano-1-methyl-guanidino)-1H-benzimidazol-1-yl]-methyl]-biphenyl-2-carboxylate and 2N sodium hydroxide solution in ethanol.

Yield: 12.9% of theory, Melting point: 182°–184° C. (sintering from 135° C.) $C_{29}H_{30}N_6O_2$ (494.61) Mass spectrum: $M^+=494$

EXAMPLE 39

4'-[[2-n-Propyl-4-chloro-6-(1-dimethylamino-2-nitro-etheneamino)-1H-benzimidazol-1-yl]-methyl]-2-(1H-tetrazol-5-yl)biphenyl-potassium salt Prepared analogously to Example 14b from 4'-[[2-n-propyl-4-chloro-6-(1-methylmercapto-2-nitro-etheneamino)-1H-benzimidazol-1-yl]-methyl]-2-(1H-tetrazol-5-yl)biphenyl and dimethylamine. The solution thus obtained is then converted into the corresponding potassium salt with potassium hydroxide solution in alcoholic solution.

Yield: 47.2% of theory, Melting point: sintering from 118° C. $C_{28}H_{27}ClKN_9O_2$ (596.16) Mass spectrum: $(M+H)^+=596/598$ Cl

EXAMPLE 40

4'-[[2-n-Propyl-4-chloro-6-(2,2-dicyano-1-dimethylamino-etheneamino)-1H-benzimidazol-1-yl]-methyl]-2-(1H-tetrazol-5-yl)-biphenyl-potassium salt Prepared analogously to Example 10d from 4'-[[2-n-propyl-4-chloro-6-(2,2-dicyano-1-methylmercapto-etheneamino)-1H-benzimidazol-1-yl]-methyl]-2-(1H-tetrazol-5-yl)biphenyl and dimethylamine in the presence of 3-chloroperoxybenzoic acid. The compound thus obtained is then converted into the corresponding potassium salt in an alcoholic solution using potassium hydroxide solution.

Yield: 52.5% of theory, Melting point: 210°–212° C. (sintering from 177° C.) $C_{30}H_{27}ClKN_{10}$ (563.09) Mass spectrum: $(M+H)^+=536/565$ Cl In the pharmaceutical examples which follow, any suitable compound of formula I may be used as active substance, but particularly those wherein $R_d$ represents a carboxy or 1H-tetrazolyl group:

EXAMPLE I

| Tablets containing 50 mg of active substance | |
|---|---|
| Active substance | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation:

The active substance, $CaHPO_4$, lactose and corn starch are uniformly moistened with an aqueous PVP solution. The mass is passed through a 2 mm screen, dried at 50° C. in a circulating air dryer and screened again.

After the lubricant has been added, the granules are compressed in a tablet making machine.

EXAMPLE II

| Coated tablets containing 50 mg of active substance | |
|---|---|
| Active substance | 50.0 mg |
| Lysine | 25.0 mg |
| Lactose | 60.0 mg |
| Corn starch | 34.0 mg |
| Gelatin | 10.0 mg |
| Magnesium stearate | 1.0 mg |
| | 180.0 mg |

Preparation:

The active substance is mixed with the excipients and moistened with an aqueous gelatin solution. After screening and drying the granules are mixed with magnesium stearate and compressed to form cores.

The cores thus produced are covered with a coating by known methods. A colouring may be added to the coating suspension or solution.

EXAMPLE III

| Coated tablets containing 100 mg of active substance | |
|---|---|
| Active substance | 100.0 mg |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation:

The active substance is mixed with the excipients and moistened with an aqueous PVP solution. The moist mass is passed through a 1.5 mm screen and dried at 45° C. After drying, it is screened again and the magnesium stearate is added. This mixture is compressed into cores.

The cores thus produced are covered with a coating by known methods. Colourings may be added to the coating suspension or solution.

EXAMPLE IV

| Capsules containing 250 mg of active substance | |
|---|---|
| Active substance | 250.0 mg |
| Corn starch | 68.5 mg |
| Magnesium stearate | 1.5 mg |
| | 320.0 mg |

Preparation:

The active substance and corn starch are mixed together and moistened with water. The moist mass is screened and dried. The dry granules are screened and mixed with magnesium stearate. The final mixture is packed into size 1 hard gelatin capsules.

EXAMPLE V

| Oral suspension containing 50 mg of active substance per 5 ml | |
|---|---|
| Active substance | 50.0 mg |
| Hydroxyethylcellulose | 50.0 mg |
| Sorbic acid | 5.0 mg |
| 70% sorbitol | 600.0 mg |
| Glycerol | 200.0 mg |
| Flavouring | 15.0 mg |
| Water ad | 5.0 ml |

Preparation:

Distilled water is heated to 70° C. Hydroxyethylcellulose is dissolved therein with stirring. With the addition of sorbitol solution and glycerol the mixture is cooled to ambient temperature. At ambient temperature, sorbic acid, flavouring and active substance are added. The suspension is evacuated with stirring to remove any air. One dose of 50 mg is contained in 5.0 ml.

EXAMPLE VI

| Suppositories containing 100 mg of active substance | |
|---|---|
| Active substance | 100.0 mg |
| Solid fat | 1600.0 mg |
| | 1700.0 mg |

Preparation:

The hard fat is melted. At 40° C. the ground active substance is homogeneously dispersed in the melt. It is cooled to 38° C. and poured into slightly chilled suppository moulds.

What is claimed is:

1. A benzimidazole of the formula I (I)

[Structure: benzimidazole with $R_a$, $R_b$ substituents on benzene ring, $R_c$ at 2-position, N-CH$_2$-biphenyl with $R_d$ on distal phenyl]

wherein $R_a$ denotes a $C_{1-3}$-alkyl group, a trifluoromethyl group, a hydrogen, fluorine, chlorine or bromine atom, $R_b$ denotes (a) a group of the formula $$-\underset{R_1}{N}-\underset{R_7}{C}=\underset{H}{C}-NO_2$$

(b) a group of the formula $$-\underset{R_1}{N}-\underset{}{C}=\underset{R}{N}-R_6, \text{ or}$$

or (c) a group of the formula

[Structure: cyclobutenedione with $R_1$N– and $R_1(R_3)$N– substituents]

R denotes a $C_{1-5}$-alkyl group, an alkoxy or alkylthio group each having 1 to 3 carbon atoms, a phenoxy or phenylthio group or an ($R_2NR_3$)—group, $R_1$ denotes a hydrogen atom or a $C_{1-3}$-alkyl group, $R_2$ denotes a hydrogen atom, a branched or unbranched $C_{1-10}$-alkyl group which may be substituted in the 2-, 3- or 4-position by a hydroxy, alkoxy, amino, alkylamino or dialkylamino group, wherein the alkyl moiety in each case may contain 1 to 3 carbon atoms, or $R_2$ denotes a $C_{1-4}$-alkyl group which is substituted by a phenyl or pyridyl group and may additionally be substituted by a hydroxy group in the 2-, 3- or 4-position, or $R_2$ denotes a $C_{3-4}$-cycloalkyl group, a $C_{5-8}$-cycloalkyl group wherein an ethylene bridge may be replaced by an o-phenylene group, or a $C_{6-8}$-bicycloalkyl group optionally substituted by 1, 2 or 3 alkyl groups, $R_3$ denotes a hydrogen atom or an alkyl group which may be substituted in the 2- or 3-position by an alkoxy, amino, alkylamino or dialkylamino group, wherein the above-mentioned alkyl and alkoxy moieties may each contain 1 to 3 carbon atoms, $R_4$ and $R_5$, which may be identical or different, each denotes a cyano, $R_2NR_3$—CO— or alkoxycarbonyl group having a total of 2 to 5 carbon atoms, wherein $R_2$ and $R_3$ are as hereinbefore defined, $R_6$ denotes a cyano, alkanesulphonyl, phenylsulphonyl, phenylalkanesulphonyl, aminosulphonyl, alkylaminosulphonyl, dialkylaminosulphonyl, alkylcarbonyl, phenylcarbonyl, aminocarbonyl, alkylaminocarbonyl or dialkylaminocarbonyl group wherein the alkyl moiety may contain 1 to 3 carbon atoms, $R_7$ denotes an ($R_2'NR_3'$)—group, wherein $R_2'$ and $R_3'$ together with the nitrogen atom between them represent a cyclic $C_{4-6}$-alkyleneimino group (which may be substituted by one or two alkyl groups or by a phenyl group and wherein additionally an ethylene bridge in the 3,4-position may be replaced by an o-phenylene group), a morpholino group or a piperazino group optionally substituted in the 4-position by a $C_{1-3}$-alkyl group or by a phenyl group, $R_c$ denotes a $C_{2-4}$-alkyl group, an alkoxy or alkylthio group each having 2 or 3 carbon atoms in the alkyl moiety, or a cyclopropyl or cyclobutyl group and $R_d$ denotes a carboxy, cyano, 1H-tetrazolyl, 1-triphenylmethyl-tetrazolyl or 2-triphenylmethyl-tetrazolyl group, or a group of the formula

—CO—OR',

—CO—O—(HCR")—O—CO—R''' or

—CO—O—(HCR")—O—CO—OR"

wherein

R' is a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, R" is a hydrogen atom or a methyl group, and R''' is a straight-chained or branched $C_{1-6}$-alkyl group, a $C_{5-7}$-cycloalkyl group, a phenyl, benzyl, 1-phenylethyl, 2-phenylethyl or 3-phenylpropyl group, or a pharmaceutically acceptable salt thereof.

2. A benzimidazole of the formula I according to claim 1 wherein $R_a$ to $R_c$ are as defined in claim 1 and $R_d$ denotes a 1H-tetrazolyl group or a carboxy group or a pharmaceutically acceptable salt thereof.

3. A benzimidazole of the formula I according to claim 1 wherein $R_a$ denotes a methyl group or a hydrogen, fluorine, chlorine or bromine atom, $R_b$ denotes (a) a group of the formula $$-\underset{R_1}{N}-\underset{R_7}{C}=\underset{H}{C}-NO_2$$

(b) a group of the formula $$-\underset{R_1}{N}-\underset{}{C}=\underset{R}{N}-R_6, \text{ or}$$

(c) a group of the formula

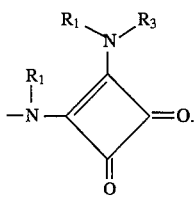

R denotes a $C_{1-3}$-alkyl group, a methoxy, methylthio, phenoxy or phenylthio group or an $(R_2NR_3)$—group, $R_1$ denotes a hydrogen atom or a $C_{1-3}$-alkyl group, $R_2$ denotes a $C_{1-3}$-alkyl group which may be substituted in the 2- or 3-position by a hydroxy, alkoxy, amino, alkylamino or dialkylamino group, whilst the alkoxy and alkyl moieties may each contain 1 to 3 carbon atoms, or $R_2$ denotes a $C_{5-7}$-cycloalkyl group, $R_3$ denotes a hydrogen atom, a $C_{1-3}$-alkyl group, a 2-methoxyethyl, 2-dimethylaminoethyl or 2-diethylaminoethyl group, $R_6$ denotes an alkylsulphonyl group having 1 to 3 carbon atoms in the alkyl moiety or a cyano, aminosulphonyl or phenylsulphonyl group, $R_2$ represents an $(R_2'NR_3')$—group, wherein $R_2'$, and $R'_3$ together with the nitrogen atom between them denote a cyclic $C_{4-5}$-alkyleneimino group which may be substituted by one or two methyl groups, morpholino group or a piperazino group optionally substituted in the 4-position by $C_{1-3}$-alkyl group, $R_c$ denotes a $C_{2-4}$-alkyl group and $R_d$ denotes a carboxy, 1H-tetrazolyl, 1-triphenylmethyl-tetrazolyl or 2-triphenylmethyl-tetrazolyl group, or a pharmaceutically acceptable salt thereof.

4. A benzimidazole of the formula I according to claim 1 wherein $R_a$ is in the 4-position and denotes a methyl group or a chlorine atom, $R_b$ is in the 6-position and denotes (a) a group of the formula

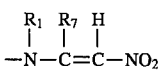

(b) a group of the formula

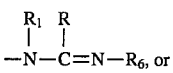

(c) a group of the formula

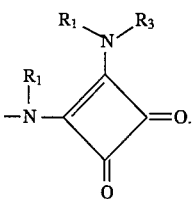

R denotes an $(R_2NR_3)$—group or a $C_{1-3}$-alkyl group, $R_1$ denotes a hydrogen atom or a methyl group, $R_2$ denotes a $C_{1-3}$-alkyl group, a 2-hydroxyethyl, 2-methoxyethyl, 2-dimethylaminoethyl or 2-diethylaminoethyl group or a $C_{5-7}$-cycloalkyl group, $R_3$ denotes a hydrogen atom, a $C_{1-3}$-alkyl group, a 2-methoxyethyl, 2-dimethylaminoethyl or 2-diethylaminoethyl group, and $R_6$ denotes a cyano, aminosulphonyl, methylsulphonyl or phenylsulphonyl group, $R_7$ denotes an $(R_2'NR_3')$—group, wherein $R_2'$ and $R_3'$ together with the nitrogen atom between them denote a pyrrolidino, piperidino, morpholino or 4-methyl-piperazino group, $R_c$ denotes a $C_{2-4}$-alkyl group and $R_d$ denotes a carboxy or 1H-tetrazolyl group, or a pharmaceutically acceptable salt thereof.

5. A benzimidazole of the formula I according to claim 1, wherein $R_a$ is in the 4-position and is a methyl group or a chlorine atom;

$R_b$ is a group of the formula

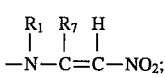

$R_1$ is a hydrogen atom or a methyl group;

$R_7$ denotes an $(R_2'NR_3')$—group, wherein $R_2'$ and $R_3'$ together with the nitrogen atom between them denote a pyrrolidino, piperidino, morpholino or 4-methyl-perazino group;

$R_c$ is a $C_{2-4}$-alkyl group; and $R_d$ is a carboxy or 1H-tetrazolyl group;

or a pharmaceutically acceptable salt thereof.

6. A benzimidazole of the formula I according to claim 1, wherein $R_a$ is in the 4-position and is a methyl group or a chlorine atom;

$R_b$ is in the 6-position and is a group of the formula

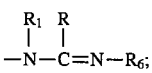

R is an $(R_2NR_3)$—group or a $C_{1-3}$-alkyl group;

$R_1$ is a hydrogen atom or a methyl group;

$R_2$ is a $C_{1-3}$-alkyl group, a 2-hydroxyethyl, 2-methoxyethyl, 2-dimethylaminoethyl or 2-diethylaminoethyl group or a $C_{5-7}$-cycloalkyl group;

$R_3$ is a hydrogen atom, a $C_{1-3}$-alkyl group, a 2-methoxyethyl, 2-dimethylaminoethyl or 2-diethylaminoethyl group;

$R_6$ is a cyano, aminosulphonyl, methylsulphonyl or phenylsulphonyl group;

$R_c$ is a $C_{2-4}$-alkyl group; and $R_d$ is a carboxy or 1H-tetrazolyl group;

or a pharmaceutically acceptable salt thereof.-

7. A benzimidazole of the formula I according to claim 1, wherein $R_a$ is in the 4-position and is a methyl group or a chlorine atom;

$R_b$ is in the 6-position and is a group of the formula

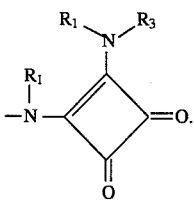

$R_1$ is a hydrogen atom or a methyl group;

$R_2$ is a $C_{1-3}$-alkyl group, a 2-hydroxyethyl, 2-methoxyethyl, 2-dimethylaminoethyl or 2-diethylaminoethyl group or a $C_{5-7}$-cycloalkyl group;

$R_3$ is a hydrogen atom, a $C_{1-3}$-alkyl group, a 2-methoxyethyl, 2-dimethylaminoethyl or 2-diethylaminoethyl group;

$R_c$ is a $C_{2-4}$-alkyl group; and $R_d$ is a carboxy or 1H-tetrazolyl group;

or a pharmaceutically acceptable salt thereof.

8. A benzimidazole selected from the group consisting of:
 (a) 4'-[[2-n-propyl-4-chloro-6-(2-cyano-3,3-dimethylguanidino)- 1H-benzimidazol -1-yl]-methyl]-2-(1H-tetrazol-5-yl)-biphenyl,
 (b) 4'-[[2-n-propyl-4-methyl-6-(2-cyano-3,3-dimethylguanidino)-1H-benzimidazol -1-yl]-methyl]-2-(1H-tetrazol-5-yl)-biphenyl,
 (c) 4'-[[2-n-propyl-4-methyl-6-[2-cyano- 3-(2-dimethylamino-ethyl) -3-methyl-guanidino]-1H-benzimidazol-1-yl]-methyl]-2-(1H-tetrazol-5-yl)-biphenyl,
 (d) 4'-[[2-n-propyl-4-methyl-6-[2-cyano-3-(2-hydroxyethyl)-3-methyl-guanidino]1H-benzimidazol-1-yl]-methyl]-2-(1H-tetrazol-5-yl)-biphenyl,
 (e) 4'-[[2-n-propyl-4-methyl-6-[2-cyano-3-(bis-2-methoxy-ethyl)-3-methyl -guanidino]-1H-benzimidazol-1-yl]-methyl]-2-(1H-tetrazol-5-yl)-biphenyl,
 (f) 4'-[[2-n-propyl-4-methyl-6-[2-cyano-3-(2-hydroxyethyl)-3-methyl-guanidino]1H-benzimidazol-1-yl]-methyl]-biphenyl-2-carboxylic acid,
 (g) 4'-[[2-ethyl-4-methyl-6-(2-cyano-3,3-dimethyl-guanidino)-1H-benzimidazol-1-yl]-methyl]-2-(1H-tetrazol-5-yl)-biphenyl,
 (h) 4'-[[2-n-propyl-4-methyl-6-(1-morpholino-2-nitroetheneamino)-1H-benzimidazol -1-yl]-methyl]-2-(1H-tetrazol-5-yl)-biphenyl, and
 (i) 4'-[[2-ethyl-4-methyl-6-[(2-dimethylamino-3,4-dioxo-1-cyclobuten-1-yl)-amino]-1H-benzimidazol-1-yl]-methyl]-2-(1H-tetrazol-5-yl)-biphenyl;
or a pharmaceutically acceptable salt thereof.

9. 4'-[[2-Ethyl-4-methyl-6-[(2-dimethylamino-3,4-dioxo-1-cyclobuten-1-yl)amino]-1H-benzimidazol-1-yl]-methyl]-2-(1H-tetrazol-5-yl)-biphenyl, or a pharmaceutically acceptable salt thereof.

10. 4'-[[2-n-Propyl-4-methyl-6-(2-cyano-3,3-dimethylguanidino)-1H-benzimidazol -1-yl]-methyl]-2-(1H-tetrazol-5-yl)-biphenyl, or a pharmaceutically acceptable salt thereof.

11. 4'-[[2-n-Propyl-4-methyl-6-(1-morpholino-2-nitroetheneamino)-1H-benzimidazol -1-yl]-methyl]-2-(1H-tetrazol-5-yl)-biphenyl, or a pharmaceutically acceptable salt thereof.

12. A pharmaceutical composition comprising a blood pressure lowering amount of a compound according to claim 1, 2, 3, 4, 5, 6, 7, 9, 10 or 11.

13. A method for lowering blood pressure which comprising administering to a host in need of such treatment a blood pressure lowering amount of a compound according to claim 1, 2, 3, 4, 5, 6, 7, 9, 10, or 11.

14. A method for the treatment of hypertension which comprising administering to a host in need of such treatment a blood pressure lowering amount of a compound according to claim 1, 2, 3, 4, 5, 6, 7, 9, 10, or 11.

* * * * *